(12) United States Patent
Hwang

(10) Patent No.: US 10,412,310 B2
(45) Date of Patent: Sep. 10, 2019

(54) IMAGE PROCESSING SYSTEM, SETTING ASSISTANCE DEVICE, AND NON-TRANSITORY COMPUTER-READABLE MEDIA

(71) Applicant: OMRON Corporation, Kyoto (JP)

(72) Inventor: Jaewook Hwang, Kyoto (JP)

(73) Assignee: OMRON Corporation, Kyoto (JP)

( * ) Notice: Subject to any disclaimer, the term of this patent is extended or adjusted under 35 U.S.C. 154(b) by 0 days.

(21) Appl. No.: 15/892,420

(22) Filed: Feb. 9, 2018

(65) Prior Publication Data

US 2019/0052789 A1 Feb. 14, 2019

(30) Foreign Application Priority Data

Aug. 10, 2017 (JP) .................. 2017-155579

(51) Int. Cl.
*H04N 5/235* (2006.01)
*H04N 5/225* (2006.01)
*G01N 21/84* (2006.01)

(52) U.S. Cl.
CPC .......... *H04N 5/2354* (2013.01); *G01N 21/84* (2013.01); *H04N 5/2256* (2013.01)

(58) Field of Classification Search
None
See application file for complete search history.

(56) References Cited

U.S. PATENT DOCUMENTS

| 5,526,094 A | * | 6/1996 | Noguchi | G03F 7/2002 |
| | | | | 355/53 |
| 2013/0064531 A1 | * | 3/2013 | Pillman | H04N 5/23296 |
| | | | | 396/62 |
| 2014/0267626 A1 | * | 9/2014 | Lilagan | H04N 5/23216 |
| | | | | 348/46 |
| 2014/0334648 A1 | * | 11/2014 | Wang | H05B 37/0272 |
| | | | | 381/150 |
| 2016/0278186 A1 | * | 9/2016 | Van De Sluis | H05B 33/0863 |
| 2016/0323972 A1 | * | 11/2016 | Bora | H05B 33/0842 |
| 2017/0097621 A1 | * | 4/2017 | Ackmann | G05B 19/0426 |
| 2017/0189640 A1 | * | 7/2017 | Sadwick | H05B 37/0272 |
| 2018/0024339 A1 | * | 1/2018 | Inomata | G02B 21/02 |
| | | | | 348/79 |
| 2018/0255616 A1 | * | 9/2018 | Pereyra | H05B 33/0845 |

FOREIGN PATENT DOCUMENTS

JP 2009128345 6/2009
JP 2015232487 12/2015

* cited by examiner

*Primary Examiner* — James M Hannett
(74) *Attorney, Agent, or Firm* — JCIPRNET

(57) ABSTRACT

Provided are a setting assistance device, an image processing system, and a setting assistance program for performing lighting-up setting of a lighting apparatus more easily. Setting assistance functions provided by an image processing apparatus include a function of presenting a plurality of lighting-up region candidates and emission state candidates to a user. The user selects a lighting-up region and an emission state from the presented candidates.

20 Claims, 18 Drawing Sheets

| IMAGE PROCESSING INFORMATION | TURN-ON REGION CANDIDATE | | | | | | | | EMISSION STATE CANDIDATE | | | |
|---|---|---|---|---|---|---|---|---|---|---|---|---|
| | TURN-ON SHAPE CANDIDATE | | | | TURN-ON SHAPE CANDIDATE | | | | | | | |
| | ALL TURNING ON | DOME SHAPE | ⋮ | DOME LOWER PART | ↑→ ←→ | ↑→ | ⋮ | ↓ | WHITE | RED | ⋮ | OFF |
| ROUGHNESS | NO | NO | ⋮ | YES | YES | YES | ⋯ | YES | YES | YES | ⋮ | OFF |
| CONTAMINATION | YES | YES | ⋮ | NO | YES | YES | ⋯ | NO | YES | YES | ⋮ | YES |
| RED | YES | YES | ⋮ | YES | YES | YES | ⋯ | YES | YES | NO | ⋮ | YES |
| ⋯ | ⋯ | ⋯ | ⋯ | ⋯ | ⋯ | ⋯ | ⋯ | ⋯ | ⋯ | ⋯ | ⋯ | ⋯ |
| REFLECTIVITY: HIGH | YES | YES | ⋮ | YES | YES | YES | ⋯ | YES | YES | YES | ⋮ | YES |
| ⋯ | ⋯ | ⋯ | ⋯ | ⋯ | ⋯ | ⋯ | ⋯ | ⋯ | ⋯ | ⋯ | ⋯ | ⋯ |

FIG. 14

IMAGE PROCESSING SYSTEM, SETTING ASSISTANCE DEVICE, AND NON-TRANSITORY COMPUTER-READABLE MEDIA

CROSS-REFERENCE TO RELATED APPLICATION

This application claims the benefit of Japan patent No. 2017-155579, filed on Aug. 10, 2017. The entirety of the above-mentioned patent application is hereby incorporated by reference herein and made a part of this specification.

BACKGROUND

Technical Field

The disclosure relates to an image processing system, a setting assistance device, and a setting assistance program for allowing lighting-up setting of a lighting apparatus to be performed.

Description of Related Art

In the factory automation (FA) field and the like, image processing technology for acquiring information about a workpiece from image data generated by photographing an object (referred to a "workpiece" hereinafter) under lighting according to light from a lighting apparatus is used.

A variety of lighting apparatuses have been developed as lighting apparatuses used in the image processing technology field. For example, Japanese Unexamined Patent Application Publication No. 2009-128345 (Patent Document 1) discloses a lighting apparatus including a plurality of lighting parts having different light colors. In addition, Japanese Unexamined Patent Application Publication No. 2015-232487 (Patent Document 2) discloses a lighting apparatus including a plurality of lighting parts having different lighting directions.

Patent Documents

A lighting apparatus which has many settable conditions such as a lighting color and a lighting direction has many lighting patterns, and when a user sets all of a lighting color, a lighting direction and the like one by one, lighting-up setting of the lighting apparatus may become complicated.

SUMMARY

According to an embodiment, a setting assistance device allowing lighting-up setting to be performed for a lighting part having a plurality of light-emitting parts arranged at positions facing a target is provided. The setting assistance device includes: a first reception means which presents a plurality of lighting-up region candidates that define one or more predetermined regions among a plurality of regions set for the plurality of light-emitting parts and accepts designation of any lighting-up region candidate; a second reception means which presents a plurality of emission state candidates that define predetermined emission states of the light-emitting parts and accepts designation of any emission state candidate; and an output means which outputs lighting-up setting of the lighting part to the lighting part on the basis of designation of a lighting-up region candidate accepted by the first reception means and designation of an emission state candidate accepted by the second reception means.

According to another embodiment, an image processing system includes: a photographing part which photographs a target; a lighting part having a plurality of light-emitting parts arranged at positions facing the target; a first reception means which presents a plurality of lighting-up region candidates that define one or more predetermined regions among a plurality of regions set for the plurality of light-emitting parts and accepts designation of any lighting-up region candidate; a second reception means which presents a plurality of emission state candidates that define predetermined emission states of the light-emitting parts and accepts designation of any emission state candidate; and an output means which outputs lighting-up settings of the lighting part to the lighting part on the basis of designation of a lighting-up region candidate accepted by the first reception means and designation of an emission state candidate accepted by the second reception means.

According to another embodiment, a setting assistance program for allowing lighting-up setting to be performed for a lighting part having a plurality of light-emitting parts arranged at positions facing a target is provided. The setting assistance program includes: a step of presenting a plurality of lighting-up region candidates that define one or more predetermined regions among a plurality of regions set for the plurality of light-emitting parts and accepting designation of any lighting-up region candidate; a step of presenting a plurality of emission state candidates that define predetermined emission states of the light-emitting parts and accepting designation of any emission state candidate; and a step of outputting lighting-up settings of the lighting part to the lighting part on the basis of the designated lighting-up region candidate and the designated emission state candidate.

BRIEF DESCRIPTION OF THE DRAWINGS

FIG. 14 is a diagram illustrating a data structure of candidate information.

DESCRIPTION OF THE EMBODIMENTS

The disclosure provides a setting assistance device, an image processing system and a setting assistance program which can allow lighting-up setting of a lighting apparatus to be performed more easily as described above.

Lighting-up setting of a lighting apparatus can be performed more easily using the setting assistance device according to an embodiment.

The above and other features, aspects and advantages of the disclosure will be apparent from the following detailed description relating to the disclosure understood in association with the attached drawings.

Hereinafter, each embodiment according to the disclosure will be described with reference to the drawings. In the following description, the same signs are attached to the same parts and components. Such parts and components also have the same names and same functions. Accordingly, detailed description thereof will not be repeated. Further, embodiments and modified examples which will be described below may be appropriately and selectively combined.

[A. Configuration of Image Processing System]

Figure 1:
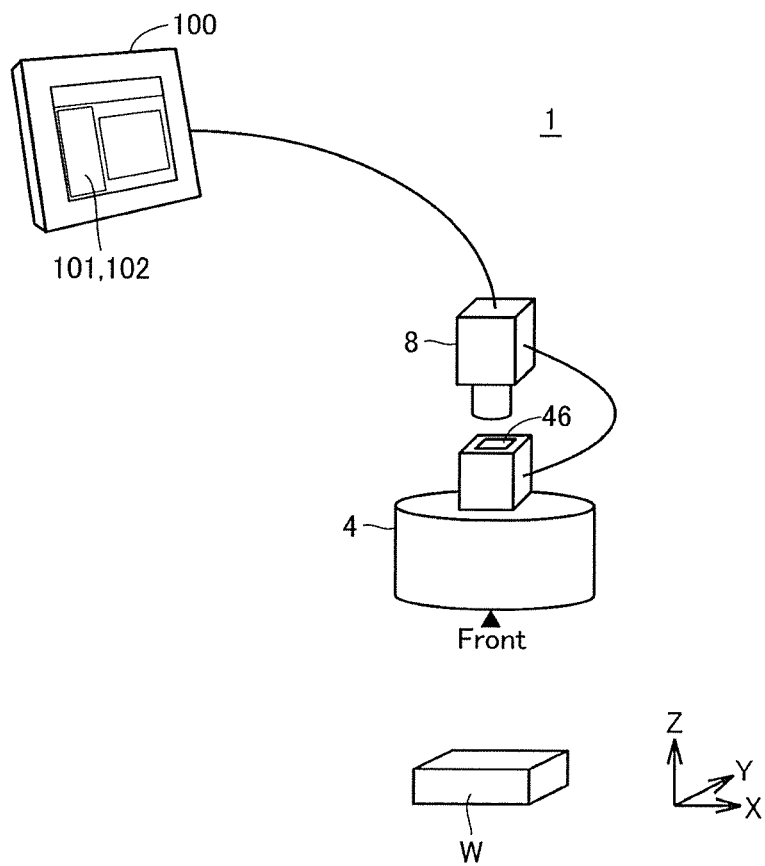
FIG. 1 is a schematic diagram illustrating a fundamental configuration of an image processing system according to embodiments of the disclosure.

FIG. 1 is a schematic diagram illustrating a fundamental configuration of an image processing system 1 according to embodiments of the disclosure. The image processing system 1 includes an image processing apparatus 100, a camera 8, and a lighting apparatus 4 as major components. The image processing apparatus 100 and the camera 8 are connected to each other such that data communication therebetween can be performed. The lighting apparatus 4 is controlled by the image processing apparatus 100 through the camera 8.

The lighting apparatus 4 is arranged such that at least part of an inspection target (referred to as a "workpiece W" hereinafter) is positioned in an irradiation region of the lighting apparatus 4. Further, when a workpiece W is carried by a carrier device such as a conveyor belt, the lighting apparatus 4 is arranged such that at least part of the carrier device is positioned in the irradiation region.

Meanwhile, a direction in which light is radiated by the lighting apparatus 4 will be defined as a Z axis, a left-to-right direction on the surface of the page is defined as an X axis, and an axis perpendicular to the X axis and the Z axis is defined as a Y axis in the following for convenience of description. In addition, light is radiated downward. Furthermore, when the position denoted by "Front" in FIG. 1 faces the lighting apparatus, the right side is regarded as the right, the left side is regarded as the left, the near side is regarded as the front, and the far side is regarded as the rear.

An opening 46 is formed on the top of the lighting apparatus 4 such that the camera 8 can photograph a workpiece W from above the lighting apparatus 4. Although the camera 8 is arranged above the lighting apparatus 4 in the present embodiment, the camera 8 may be arranged such that at least part of the irradiation region of the lighting apparatus 4 is included in at least part of the photographing field of view of the camera 8 or the camera 8 may be arranged at the side of the lighting apparatus 4.

The camera 8 is a photographing part which photographs a subject present in the photographing field of view to generate image data. The camera 8 includes an optical system such as lenses and a diaphragm, and a light-receiving element such as a charge coupled device (CCD) image sensor or a complementary metal oxide semiconductor (CMOS) image sensor as major components.

The image processing apparatus 100 can accept setting of details of image processing and further executes image processing including inspection for the presence or absence of defects or contamination on a workpiece W, measurement of the size, arrangement and orientation and the like of the workpiece W, and recognition of characters and figures on the surface of the workpiece W. Setting of details of image processing includes setting of photographing conditions when image data is acquired, and setting of details of processing executed on the image data. Setting of photographing conditions includes lighting-up setting for the lighting apparatus 4 and camera setting for the camera 8. The image processing apparatus 100 serves as a setting assistance device which allows lighting-up setting to be performed for the lighting apparatus 4. Further, a setting assistance device which allows lighting-up setting to be performed for the lighting apparatus 4 may be provided separately from the image processing apparatus 100.

The image processing apparatus 100 includes a display part 101 and a touch panel 102 mounted on the surface of the display part 101. Typically, the display part 101 is a liquid crystal display and displays details of settings to a user, for example. The touch panel 102 serves as an input part for inputting information about various settings. For example, a user can input setting information about setting of details of image processing by operating the touch panel 102 on the basis of information displayed on the display part 101. Although the input part is configured as a touch panel, but the input part may be configured as a keyboard, a mouse or both thereof.

[B. Configuration of Lighting Apparatus]

Figure 2:
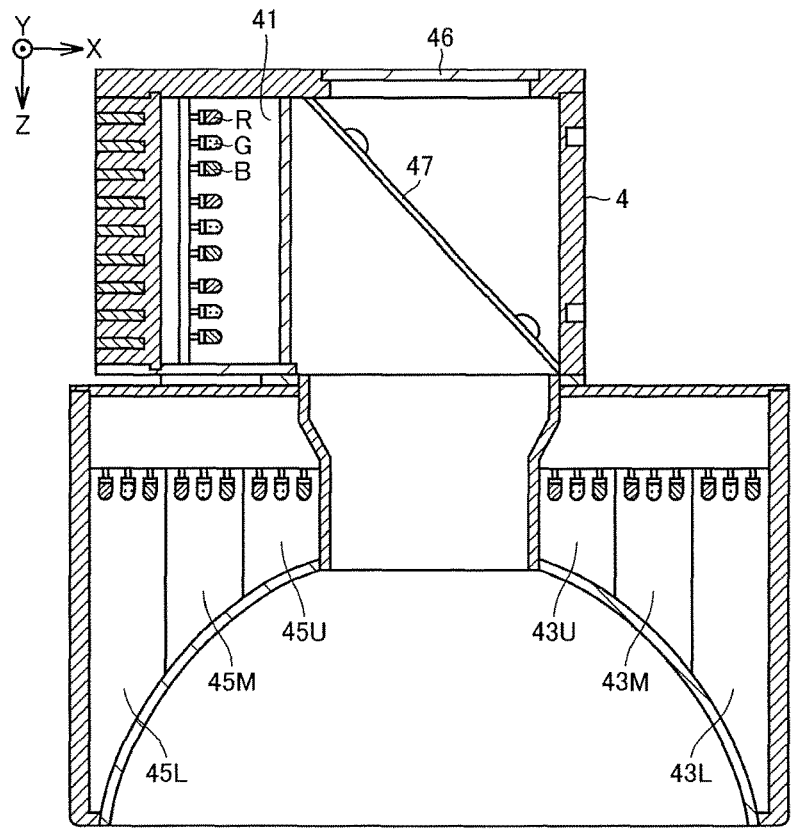
FIG. 2 is a cross-sectional view of a lighting apparatus.
Figure 3:
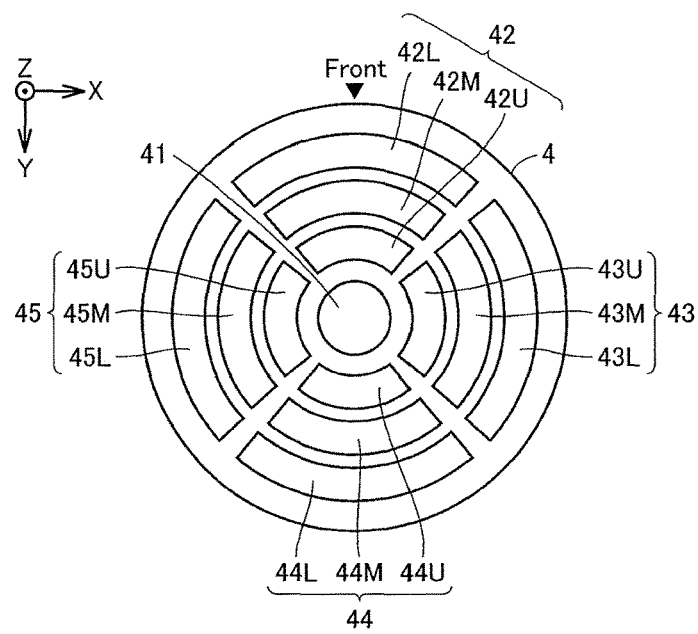
FIG. 3 is a bottom view of the lighting apparatus.

A configuration of the lighting apparatus 4 will be described with reference to FIGS. 2 and 3. FIG. 2 is a diagram illustrating an XY cross section of the lighting apparatus 4 and FIG. 3 is a bottom view of the lighting apparatus 4.

In FIG. 2, the XZ cross section of the lighting apparatus 4 is viewed from the position denoted by "Front" in FIG. 1. As shown in FIG. 2, lighting of the lighting apparatus 4 has a dome shape. In the lighting apparatus 4, light-emitting parts of a plurality of types (also referred to as "light sources" hereinafter) having different dominant wavelengths are arranged in a plurality of sets at a position facing a workpiece W. Specifically, a plurality of sets each of which is composed of a red light source R, a green light source G and a blue light source B are arranged. In FIG. 2, a light source represented by left downward slant lines is the red light source R, a light source represented by a dot pattern is the green light source G, and a light source represented by right downward slanted lines is the blue light source B, and some signs are omitted.

The plurality of light sources are divided into a plurality of regions. Specifically, a circular central region 41 (referred to as a "circular region" hereinafter), and an arc-shaped front region 42, an arc-shaped right region 43, an arc-shaped rear region 44 and an arc-shaped left region 45, which are arranged around the central region 41, are set for a lighting-up region of each set of the plurality of light sources arranged in the lighting apparatus 4.

Lights radiated from the central region 41, the front region 42, the right region 43, the rear region 44 and the left region 45 have different incident azimuths. The incident azimuth is an azimuth having the Z axis as a center. In addition, the front region 42, the right region 43, the rear region 44 and the left region 45 form a ring shape having the central region 41 as a center. Although a ring-shaped region having the central region 41 as a center is divided into four regions in the present embodiment, the ring-shaped region may be divided into more than four or equal to or less than three regions. Meanwhile, light radiated from the central region 41 is reflected by the reflector 47 and radiated downward.

In addition, a plurality of ring-shaped regions having different diameters with the circular central region 41 as a center (referred to as "ring-shaped regions" hereinafter) are set for the lighting-up regions of each set of the plurality of light sources. Specifically, an upper region, a middle region and a lower region are set. Each of the upper region, the middle region and the lower region is composed of a plurality of arc regions. For example, the upper region is composed of a front region upper part 42U, a right region upper part 43U, a rear region upper part 44U and a left region upper part 45U. In the same manner, the middle region is composed of a front region middle part 42M, a right region middle part 43M, a rear region middle part 44M and a left region middle part 45M, and the lower region is composed of a front region lower part 42L, a right region lower part 43L, a rear region lower part 44L and a left region lower part 45L. Lights radiated from ring-shaped regions having different diameters enter the XY plane at different incident angles. Meanwhile, although three ring-shaped regions are set here, two or more than three ring-shaped regions may be set.

The plurality of light sources provided in the lighting apparatus 4 according to the present embodiment are divided into 13 regions. The lighting apparatus 4 can adjust emission states of the light sources for each of the 13 regions provided therein. Here, an emission state of a light source includes not only being turned on or turned off but also a color or intensity of light radiated from a region.

Furthermore, the same number of red light sources R, green light sources G and blue light sources B need not be arranged in each region, and one or more of each type of light sources may be arranged. In addition, the proportion of red light sources R, green light sources G and blue light sources B included in each region may be identical or different. For example, more red light sources R than other light sources may be arranged in one region, whereas fewer red light sources R than other light sources may be arranged in other regions.

For example, the lighting apparatus 4 may turn on only light sources included in the front region lower part 42L and turn off all light sources included in the remaining regions. In this manner, the lighting apparatus 4 may adjust emission states of light sources for each region. Accordingly, it is possible to radiate light to a workpiece W from the top, front, right, rear or left. That is, the lighting apparatus 4 may radiate light at different incident azimuths. In addition, the lighting apparatus 4 may radiate light at different incident angles because the light sources are divided into a plurality of ring-shaped regions having different diameters. Furthermore, when the lighting apparatus 4 turns on light sources of regions, the lighting apparatus 4 may change the emission intensity for light sources having different dominant wavelengths and turn on these light sources. Accordingly, the lighting apparatus 4 can change colors of light radiated to a workpiece W.

[C. Hardware Configuration of Image Processing Apparatus 100]

Figure 4:
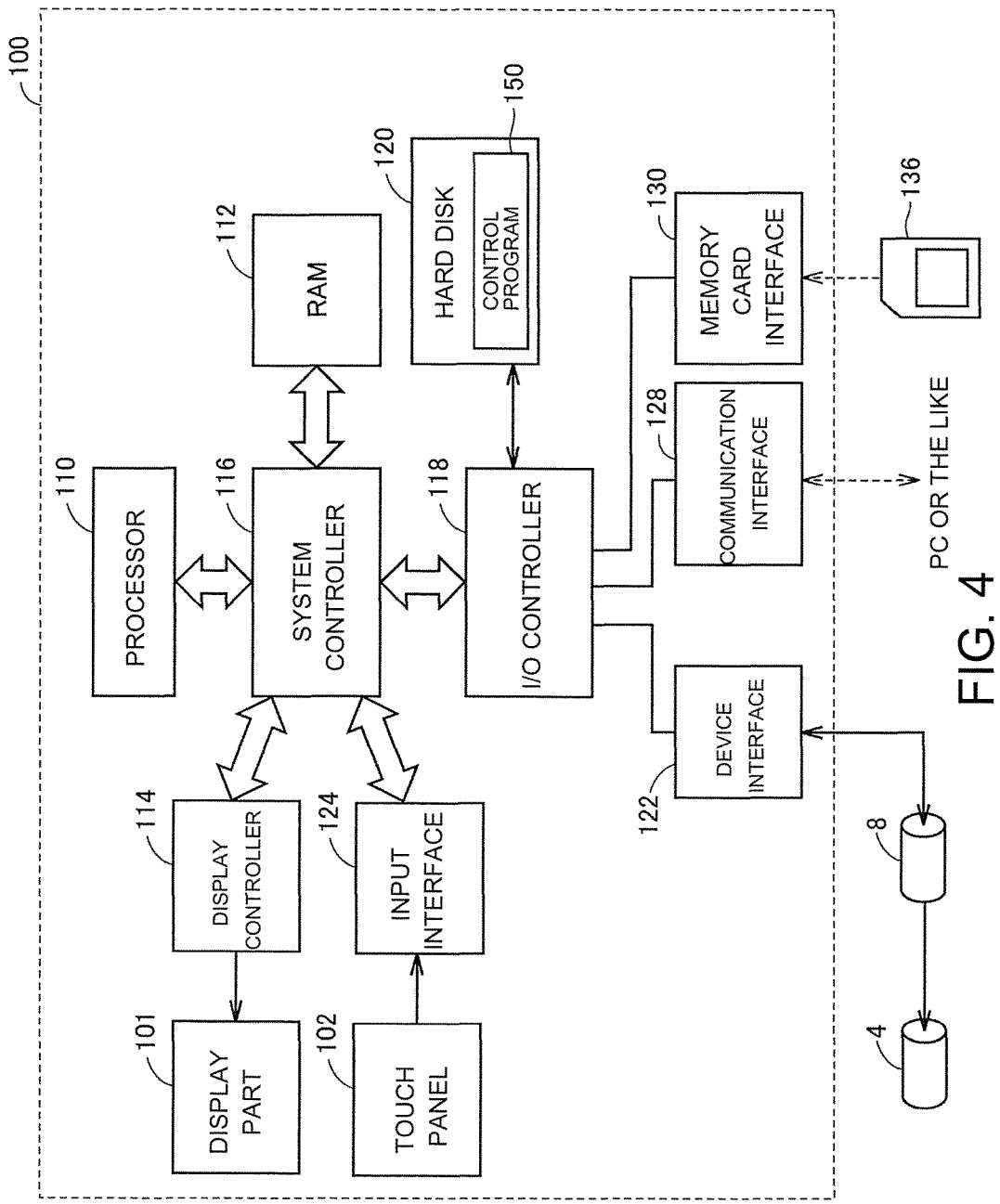
FIG. 4 is a schematic diagram illustrating a hardware configuration of an image processing apparatus.

FIG. 4 is a schematic diagram illustrating a hardware configuration of the image processing apparatus 100. As shown in FIG. 4, the image processing apparatus 100 typically has a structure according to a general computer architecture and realizes various processes as will be described later by executing previously installed programs through a processor.

More specifically, the image processing apparatus 100 includes a processor 110 such as a central processing part (CPU) or a micro-processing part (MPU), a random access memory (RAM) 112, a display controller 114, a system controller 116, an input/output (I/O) controller 118, hard disk 120, a device interface 122, an input interface 124, a communication interface 128, and a memory card interface 130. These components are connected having the system controller 116 as the center such that they can communicate with one another.

The processor 110 realizes a target operation process by exchanging programs (codes) with the system controller 116 and executing the programs in a predetermined order.

The system controller 116 is connected to the processor 110, the RAM 112, the display controller 114, the input interface 124 and the I/O controller 118 via a bus, performs exchange of data with each component, and the like and is in charge of overall processing of the image processing apparatus 100.

The RAM 112 is typically a volatile storage device such as a dynamic random access memory (DRAM) and keeps programs read from the hard disk 120, camera images (image data) captured by the camera 8, image data processing results, work data including photographing conditions, and the like.

The display controller 114 is connected to the display part 101 and outputs signals for displaying various types of information to the display part 101 according to an internal command from the system controller 116.

The input interface 124 is connected to the touch panel 102 and transmits various types of information input through the touch panel 102 to the system controller 116.

The I/O controller 118 controls data exchange with a recording medium or an external device connected to the image processing apparatus 100. More specifically, the I/O controller 118 is connected to the hard disk 120, the device interface 122, the communication interface 128 and the memory card interface 130.

The hard disk 120 is typically a non-volatile magnetic storage device and stores various setting values and the control program 150 such as algorithms executed in the processor 110. The control program 150 installed in the hard disk 120 is distributed in a state of being stored in the memory card 136 or the like. Meanwhile, a semiconductor storage device such as a flash memory or an optical storage device such as a digital versatile disk random access memory (DVD-RAM) may be employed instead of the hard disk 120.

The device interface 122 mediates data transmission between the camera 8 and the lighting apparatus 4 and the processor 110. The device interface 122 outputs an instruction from the processor 110 according to photographing conditions to the camera 8 and the lighting apparatus 4 through the device interface 122. In addition, the device interface 122 acquires image data obtained by photographing a workpiece W and mediates data transmission between the processor 110 and the camera 8.

The communication interface 128 mediates data transfer between the processor 110 and another personal computer, a server device or the like which is not shown. The communication interface 128 is typically configured using Ethernet (registered trademark), a universal serial bus (USB) or the like.

The memory card interface 130 mediates data transfer between the processor 110 and the memory card 136 which is a computer readable recording medium. The memory card 136 is distributed in a state in which the control program 150 and the like executed in the image processing apparatus 100 has been stored, and the memory card interface 130 reads the control program from the memory card 136. The memory card 136 is a general semiconductor storage device such as secure digital (SD), a magnetic recording medium such as a flexible disk, or an optical recording medium such as a compact disk read only memory (CD-ROM). Alternatively, a program downloaded from a distribution server or the like may be installed in the image processing apparatus 100 through the communication interface 128.

When a computer having the above-described structure according to a general computer architecture is used, an operating system (OS) for providing fundamental functions of the computer may be installed in addition to applications for providing functions according to the present embodiment. In this case, the control program according to the present embodiment may call necessary modules among program modules provided as part of the OS in a predetermined order and/or at predetermined timings and execute processing.

Further, the control program according to the present embodiment may be provided by being combined with another program. In this case, the program does not include modules included in the other program with which the program is combined and executes processing in cooperation with the other program. That is, the control program according to the present embodiment may be combined with other programs.

Alternatively, some or all of functions provided through execution of the control program may be realized using a dedicated hardware circuit.

[D. Overview]

The lighting apparatus 4 according to the present embodiment includes a plurality of light sources of a plurality of types having different dominant wavelengths. In addition, the plurality of light sources are divided into a plurality of regions. The lighting apparatus 4 may adjust emission states of the light sources for each region. Accordingly, a user can select a region to be turned on from the plurality of regions and select emission intensities of various light sources included in the turned on region to thereby select various lighting patterns.

In image processing, there is an appropriate lighting pattern depending on details of image processing. For example, when the user detects defects generated in a workpiece W, dust attached to the surface of the workpiece W, or the like, the user may select a lighting pattern of a low angle which can emphasize coarseness of the surface of the workpiece W. In addition, the user may increase the sensitivity for detecting defects or dust by adjusting the color of lighting on the basis of the color of the workpiece. Accordingly, it is important to select an appropriate lighting pattern depending on details of image processing in image processing.

The lighting apparatus 4 according to the present embodiment can radiate light to a workpiece W using various lighting patterns and thus can radiate lighting patterns corresponding to various image processes. On the other hand, it takes time for the user to select a lighting pattern because there are many selectable lighting patterns. The image processing apparatus according to the present embodiment has setting assistance functions of assisting lighting-up setting for selecting a lighting pattern, which can reduce man-hours required to select a lighting pattern.

Figure 5:
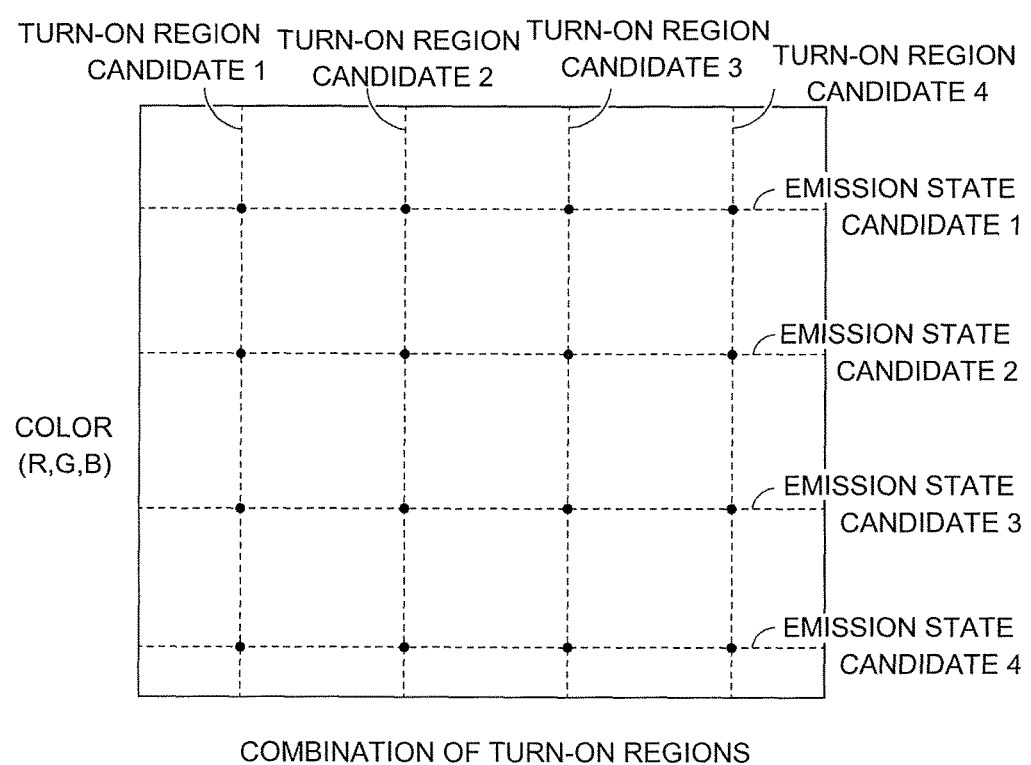
FIG. 5 is an image diagram of a setting assistance function provided by the image processing apparatus.

An overview of the setting assistance functions provided by the image processing apparatus 100 according to the present embodiment will be described with reference to FIG. 5. FIG. 5 is an image diagram of the setting assistance functions provided by the image processing apparatus 100. The horizontal axis of the graph shown in FIG. 5 represents colors of light which can be radiated from the lighting apparatus 4. Specifically, the horizontal axis represents a combination of the emission intensity of a red light source, the emission intensity of a green light source and the emission intensity of a blue light source. The vertical axis represents a combination of turned-on regions. Here, since the plurality of light sources of the lighting apparatus 4 are divided into 13 regions in the present embodiment, the number of combinations of lighting-up regions and turn-off regions is 8192 corresponding to $2^{13}$.

The setting assistance functions provided by the image processing apparatus 100 include a function of presenting a plurality of lighting-up region candidates and a plurality of emission state candidates to the user. The user selects a lighting-up region and an emission state from the presented candidates. In this manner, candidates to be selected are presented and thus the user can easily perform lighting-up setting.

Hereinafter, specific methods for realizing the setting assistance functions will be described on the basis of the function of presenting a plurality of lighting-up region candidates and a plurality of emission state candidates.

[E. User Interface 300 in Which Candidates to be Selected are Presented]

Figure 6:
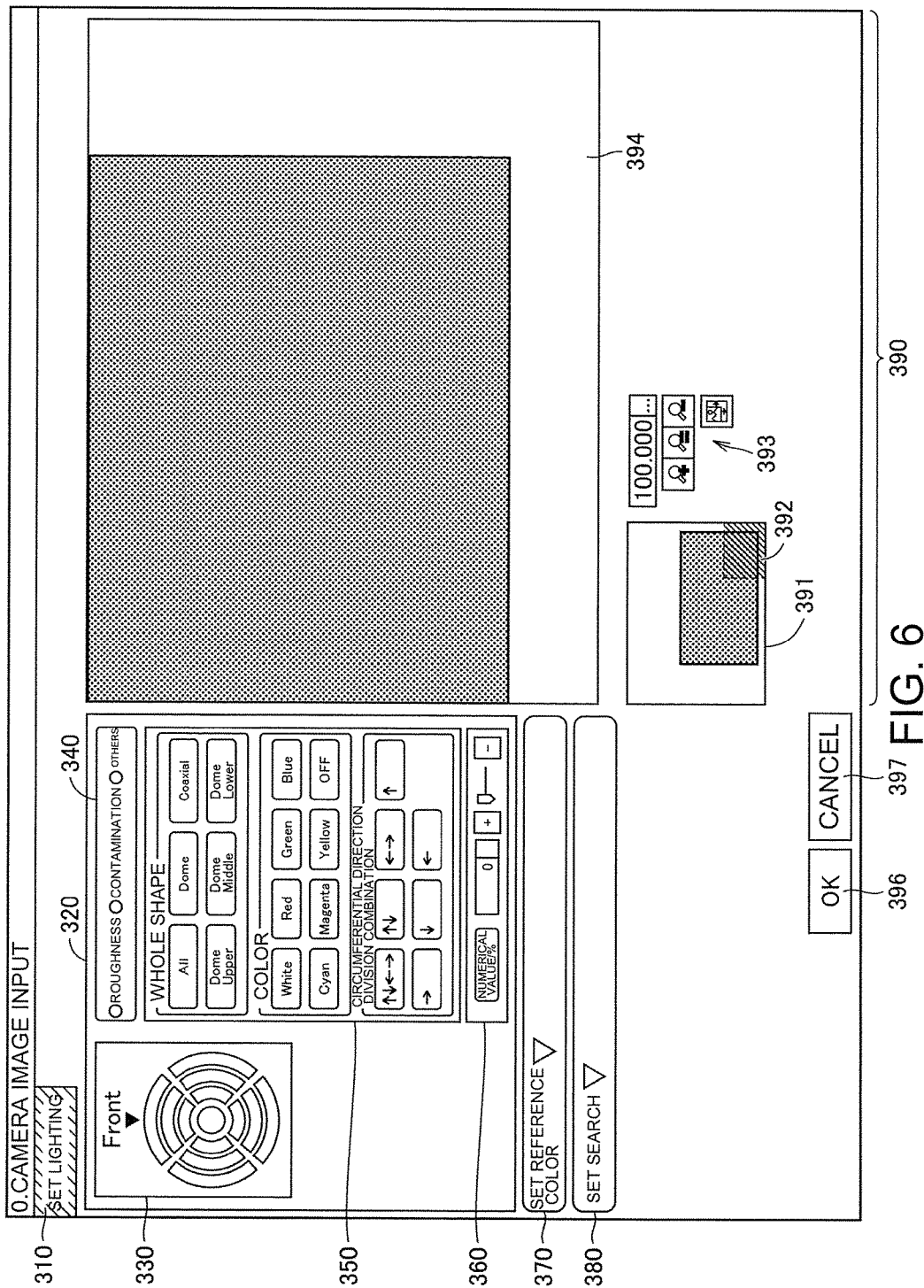
FIG. 6 is a diagram illustrating a user interface for allowing lighting-up setting of a lighting apparatus to be performed.
Figure 7:
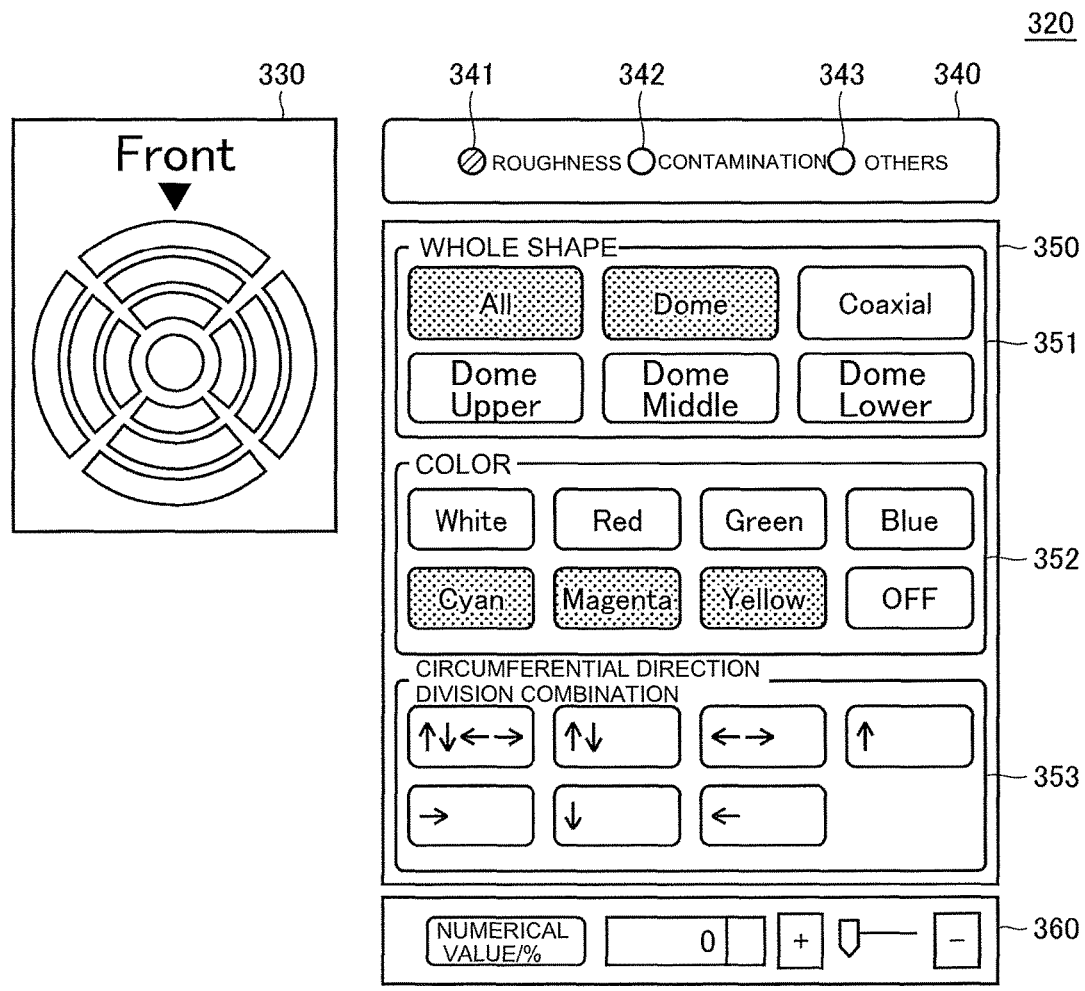
FIG. 7 is a diagram illustrating a reception region of a step in which details of image processing are input.
Figure 8:
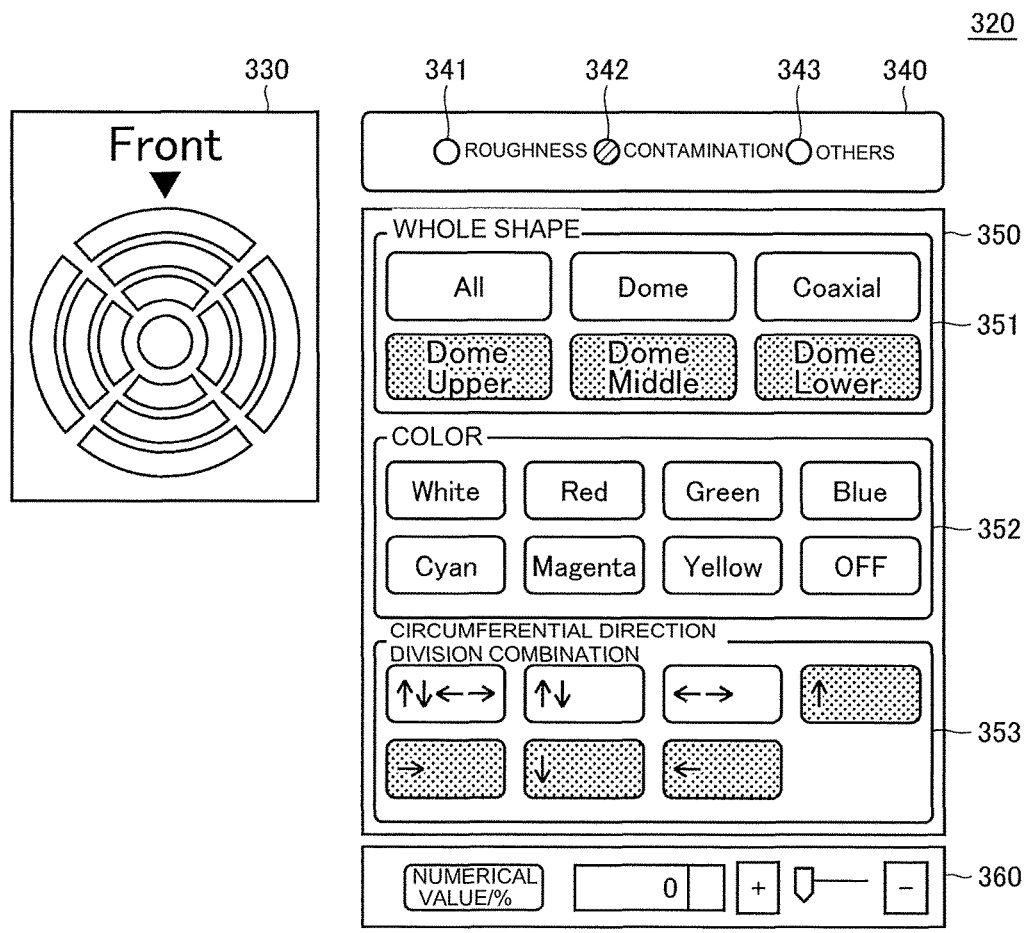
FIG. 8 is a diagram illustrating a reception region of a step in which details of image processing are input.
Figure 9:
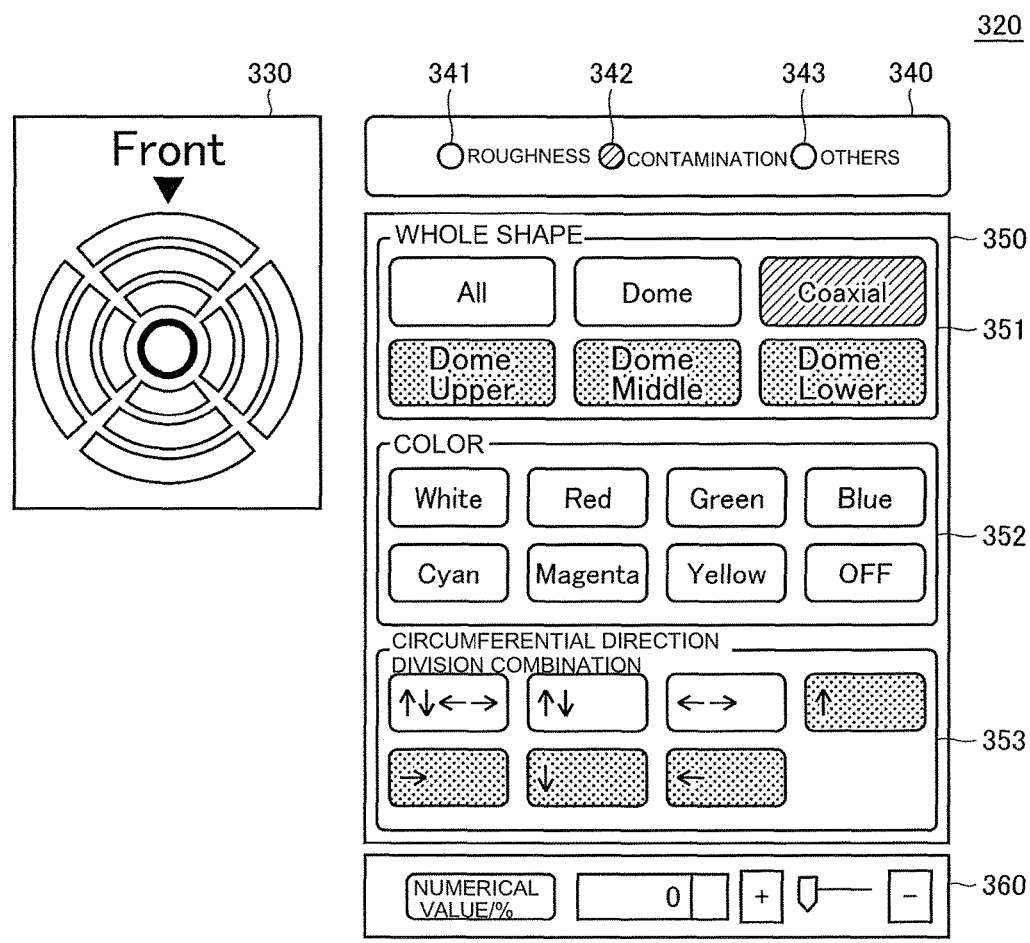
FIG. 9 is a diagram illustrating a reception region in a step in which a region is selected.
Figure 10:
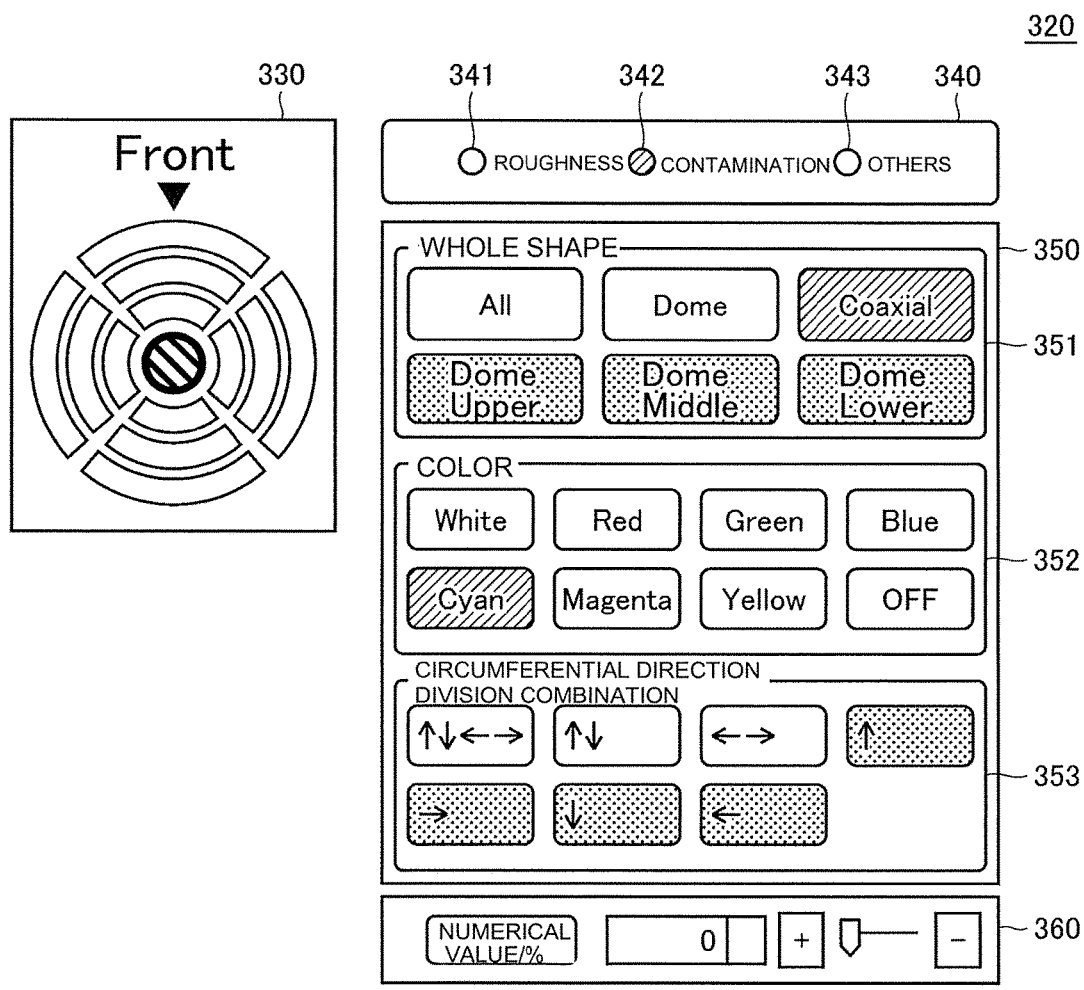
FIG. 10 is a diagram illustrating a reception region in a step of adjusting an emission intensity of a selected region.

A user interface 300 in which candidates to be selected are presented, which is provided by the image processing apparatus 100, will be described with reference to FIGS. 6 to 10. FIG. 6 is a diagram illustrating the user interface 300 for allowing lighting-up setting to be performed for the lighting apparatus 4. FIGS. 7 and 8 are diagrams illustrating a reception region in a step in which details of image processing are input. FIG. 9 is a diagram illustrating a reception region in a step in which a region is selected. FIG. 10 is a diagram illustrating a reception region in a step of adjusting the emission intensity of a selected region.

The user interface 300 for allowing lighting-up setting to be performed for the lighting apparatus 4 shown in FIG. 6 is displayed on the display part 101 when a lighting-up setting tab 310 is selected. Although tabs other than the lighting-up setting tab 310 are omitted in FIG. 6, tabs related to other settings, such as a "camera setting" tab for allowing setting for the camera 8 to be performed and an "image process setting" tab for allowing setting of details of processing executed on acquired image data to be performed may be further provided.

"Lighting-up setting" is selection of a lighting pattern of the lighting apparatus 4 among settings for the lighting apparatus 4. Specifically, lighting-up setting includes setting of regions to be turned on among a plurality of regions and setting of emission intensities of various light sources having different dominant wavelengths. The color and intensity of light radiated from the lighting apparatus are determined by setting emission intensities of various light sources having different dominant wavelengths.

The user interface 300 includes a reception region 320, a reference color setting region 370, a search setting region 380, an OK button 396, a cancel button 397, and a lighting-up state confirmation region 390.

The reception region 320 includes a setting details display region 330 in which details of settings are graphically displayed, an image processing details reception region 340 which accepts designation of an image processing type, a candidate selection region 350, and a luminance adjustment region 360.

A plurality of lighting-up region candidates and a plurality of emission state candidates are presented in the candidate selection region 350. Designation of a type of processing for an image is accepted by selecting one of buttons included in the image processing details reception region 340. The image processing apparatus 100 determines lighting-up region candidates and emission state candidates to be presented on the basis of the designated type of processing for the image.

The user can change luminances of all light sources at the same rate by operating an icon included in the luminance adjustment region 360 irrespective of light source type.

Selection of a region is accepted in such a manner that the user selects one of the plurality of lighting-up region candidates presented in the candidate selection region 350. In addition, designation of the emission intensity of each type of light sources of a plurality of types having different dominant wavelengths is accepted in such a manner that the user selects one of the plurality of emission state candidates presented in the candidate selection region 350. When a lighting-up region candidate and an emission state candidate included in the candidate selection region 350 are selected, details of the selected candidates are reflected in the setting details display region 330.

A button for setting a color of lighting using image data is provided in the reference color setting region 370. The image processing apparatus 100 may display or may not display various buttons provided in the reference color setting region 370 in response to user operations.

A button for searching for an emission state in which a contrast between two regions within image data is maximized is provided in the search setting region 380. The image processing apparatus 100 may display or may not display various buttons provided in the search setting region 380 in response to user operations.

When the OK button 396 is operated, information indicating selected lighting-up setting is saved and stored in the RAM 112. When the cancel button 397 is operated, the information indicating selected lighting-up settings is discarded without being stored in the RAM 112.

After the OK button 396 is operated, various light sources may be set for a region different from the set region. When emission intensities of light sources are changed for each region, lighting-up setting may be performed for each region set to the same emission intensity. For example, first lighting-up setting for determining an emission intensity for a first region may be performed, and then second lighting-up setting for determining an emission intensity for a second region may be performed.

Image data acquired from the camera 8 is displayed in the lighting-up state confirmation region 390. An image displayed in the lighting-up state confirmation region 390 is updated in real time. When the user performs lighting-up setting by operating various buttons or various icons included in the reception region 320, the processor 110 of the image processing apparatus 100 instructs the lighting apparatus 4 to be turned on according to details of the performed lighting-up setting. That is, the processor 110 updates lighting-up settings of the lighting apparatus 4 in real time. As a result, image data when the lighting apparatus is controlled according to lighting-up setting performed by the user by operating various buttons or various icons included in the reception region 320 is displayed in the lighting-up state confirmation region 390.

The lighting-up state confirmation region 390 includes an overall display region 391, a display control icon group 393, and an image display region 394. Image data acquired from the camera 8 is displayed in the overall display region 391 and the image display region 394. Overall target image data is displayed in the overall display region 391 independently of a display range in the image display region 394. An image of a display range 392 displayed in the image display region 394 is displayed in the overall display region 391. The display range 392 is changed in response to user operations (enlargement or reduction) on the display control icon group 393, and a display range and display accuracy of image data displayed in the image display region 394 are changed in response to user operations on the display control icon group 393.

Various buttons provided in the candidate selection region 350 will be described with reference to FIG. 7. The candidate selection region 350 includes a lighting-up shape candidate presentation region 351 and a lighting-up direction candidate presentation region 353 for presenting lighting-up region candidates, and a color candidate presentation region 352 for presenting emission state candidates.

The lighting-up shape candidate presentation region 351 is a region for presenting lighting-up region candidates determined by the central region 41 and a plurality of ring-shaped regions (upper region, middle region and lower region) which have different diameters and provided having the central region 41 as the center. For example, "All" represents lighting-up region candidates which determine turning on of a circular region and a plurality of ring-shaped regions. In addition, "Dome" represents lighting-up region candidates which determine turning on of a plurality of ring-shaped regions. When the "Dome" button is pressed, designation of an upper region group corresponding to ring-shaped regions having a longest diameter, a middle region group corresponding to ring-shaped regions having a middle diameter, and a lower region group corresponding to ring-shaped regions having a shortest diameter is accepted. In addition, when a "Coaxial" button is pressed, designation of the central region 41 is accepted.

The lighting-up direction candidate presentation region 353 is defined by regions divided in the circumferential direction and presents lighting-up region candidates. In the present embodiment, a ring-shape region is divided into four regions in the circumferential direction and each region has an arch shape. Combinations of the divided four regions are presented as lighting-up region candidates in the lighting-up direction candidate presentation region 353. For example, a button on which "upward arrow, downward arrow, right arrow and left arrow" is indicated is a lighting-up region candidate which represents selection of all of the four regions. Designation of a lighting-up region candidate is accepted when the user selects one of various buttons included in the lighting-up direction candidate presentation region 353.

The image processing apparatus 100 determines a duplicated lighting-up region candidate among lighting-up region candidates designated by performing operations on the lighting-up shape candidate presentation region 351 and lighting-up region candidates designated by performing operations on the lighting-up direction candidate presentation region 353 as a lighting-up region of a setting target. Further, when only one of the lighting-up shape candidate presentation region 351 and the lighting-up direction candidate presentation region 353 has been operated, the image processing apparatus 100 determines a lighting-up region candidate designated by performing operations on the region as a setting target.

A plurality of emission state candidates which specify emission states of light sources are presented in the color candidate presentation region 352. In the present embodiment, a plurality of colors specified by the emission intensity of each light source type are presented in the color candidate presentation region 352.

The user may select one of details of image processing presented in the image processing details reception region 340. The image processing apparatus 100 determines selection candidates to be presented in the candidate selection region 350 depending on details of image processing selected by the user.

In FIG. 7, it is assumed that the user selects detection of roughness of a workpiece W as details of image processing. Dot patterns in FIG. 7 mean details which are not included in selection candidates and thus cannot be selected by the user. That is, when detection of roughness of the workpiece W is designated, "ALL" and "Dome" cannot be selected. In addition, "Cyan," "Magenta" and "Yellow" cannot be selected as colors of light radiated from the lighting apparatus 4.

In FIG. 8, it is assumed that the user selects detection of contamination of the workpiece W as details of image processing. In this case, "Dome Upper," "Dome Middle," "Dome Lower" and an irradiation pattern from one direction cannot be selected.

Meanwhile, when the user selects "Others," all buttons can be selected. Furthermore, although only two types of details of image processing are disclosed in the present embodiment, selection candidates depending on types of workpieces W may be provided.

In addition, although an example in which candidates which are not presented are represented using a dot pattern is given in the present embodiment, candidates which are not presented may not be displayed in the first of all.

When one of a plurality of lighting-up region candidates has been selected, the selected region is displayed in a different state from other regions in the setting details display region 330, as shown in FIG. 9. Although FIG. 9 illustrates an example in which the selected region is displayed such that is can be recognized between the selected region and unselected regions by indicating the selected region with a thick line, the display manner is not limited to the manner shown in FIG. 9 and any display manner in which the selected region can be recognized by the user may be employed.

After the region has been selected, when a button included in the color candidate presentation region 352 is operated to select one emission state candidate, the selected region is displayed in the selected color in the setting details display region 330. FIG. 10 illustrates an example in which "Cyan" has been selected, and the selected region is displayed in cyan in the setting details display region 330.

[G. User Interface 300 when Emission State is Adjusted Through Image Data]

Figure 11:
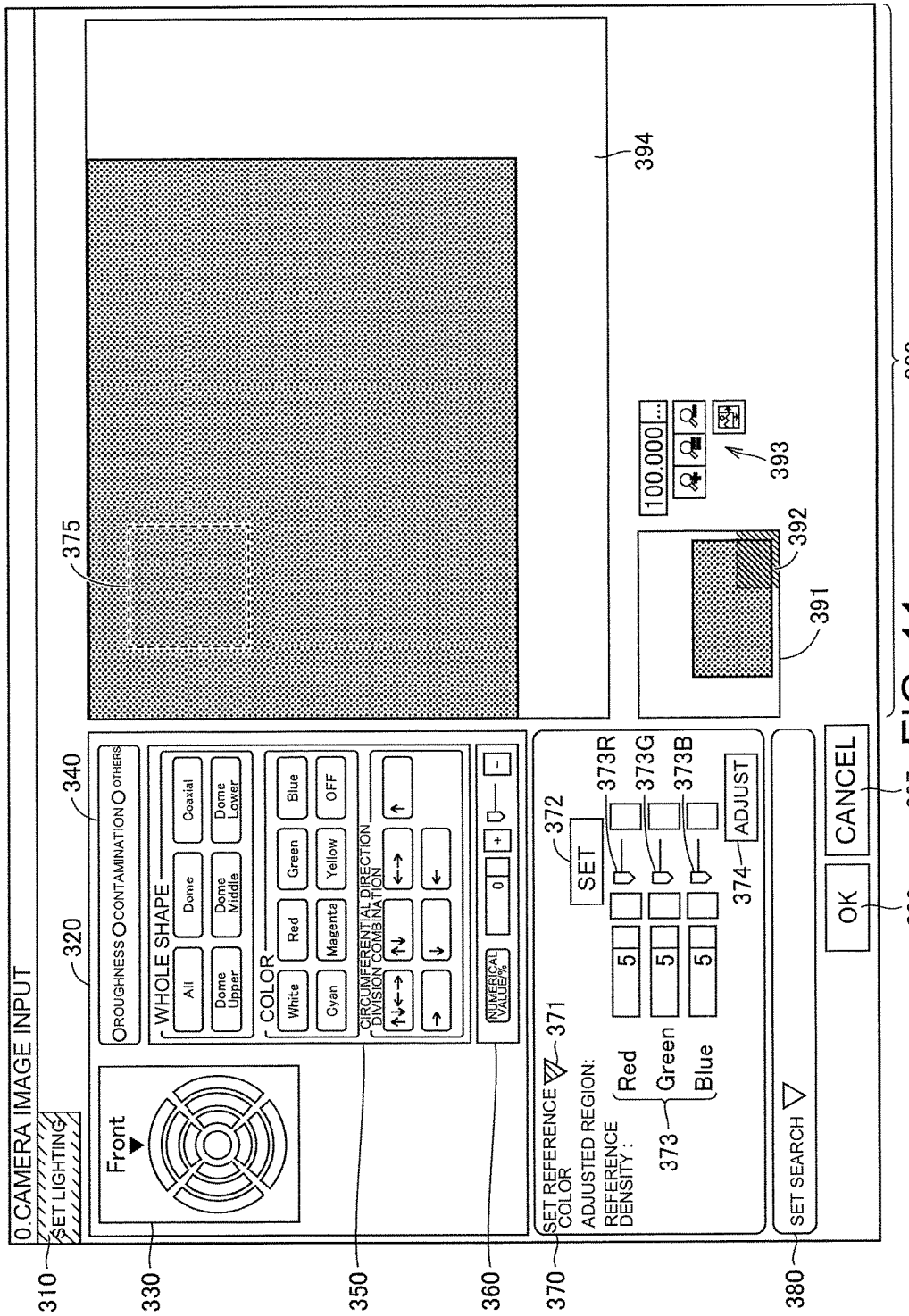
FIG. 11 is a diagram illustrating an example of a user interface for setting a color of lighting using image data.
Figure 12:
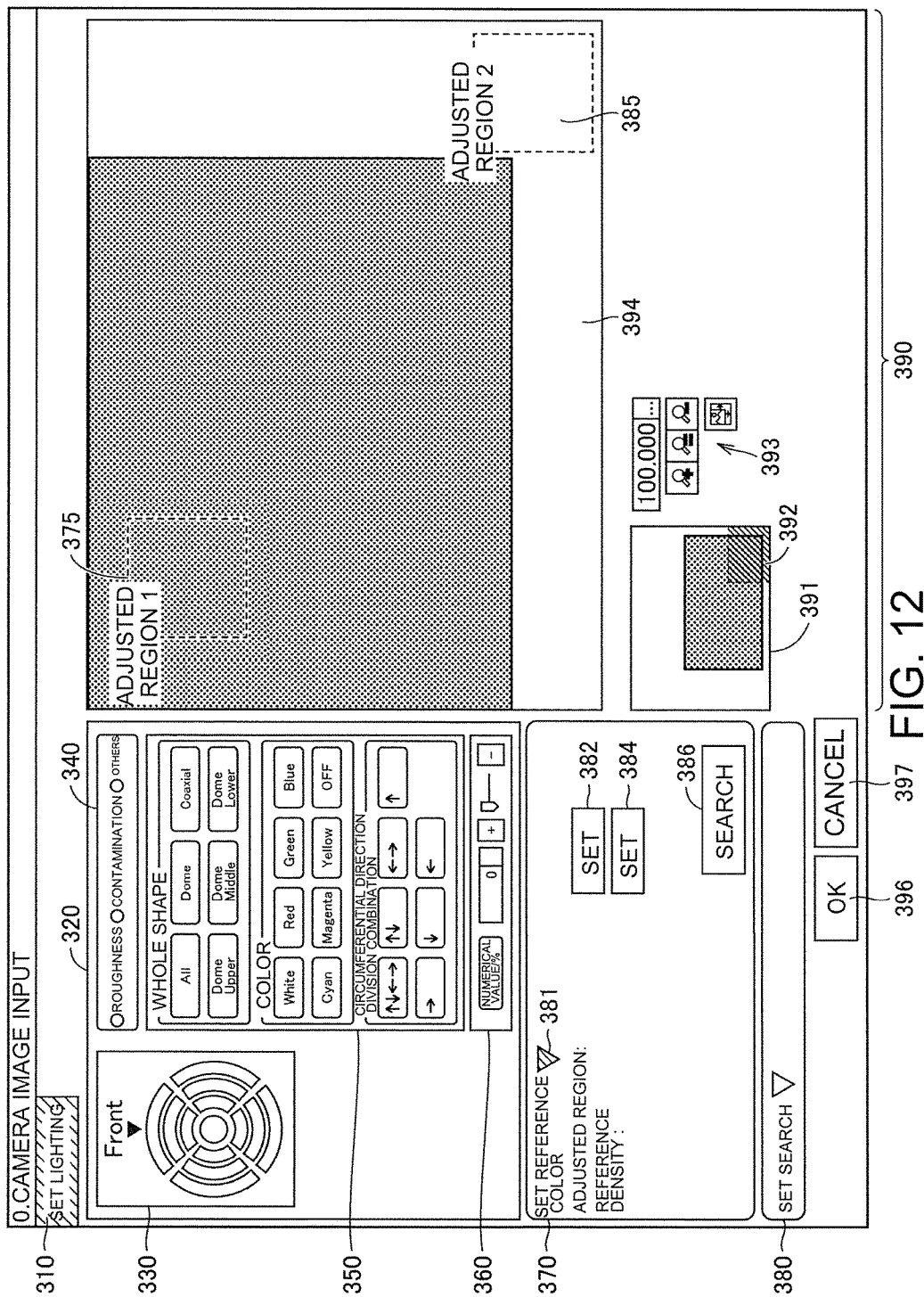
FIG. 12 is a diagram illustrating an example of a user interface for searching for a setting for maximizing contrast.

The user interface 300 when setting of the lighting apparatus 4 is adjusted through image data will be described with reference to FIGS. 11 and 12. FIG. 11 is a diagram illustrating an example of a user interface for setting a color of lighting using image data. FIG. 12 is a diagram illustrating an example of a user interface for searching for setting for maximizing contrast.

The image processing apparatus 100 may display image data captured by the camera 8 on the display part 101. The image processing apparatus 100 may adjust the emission state of light radiated from the lighting apparatus 4 through image data captured by the camera 8 as a setting assistance function.

The image processing apparatus 100 mainly has three adjustment functions. The first adjustment function is a function of adjusting input luminance information to correspond to luminance information extracted from image data. The second adjustment function is a function of adjusting luminance information of each color extracted from image data to be constant. The third adjustment function is a function of searching for luminance information which maximizes the contrast between two regions in image data and adjusting an emission state depending on the search result.

A user interface for realizing the aforementioned first and second adjustment functions will be described with reference to FIG. 11.

The reference color setting region 370 includes a display switch icon 371, a region setting button 372, a luminance information input region 373, and an adjustment initiation button 374.

The display switch icon 371 is an icon for switching display and non-display of the region setting button 372, the luminance information input region 373 and the adjustment initiation button 374.

The region setting button 372 is a button for setting a region from which luminance information is extracted in image data. When the region setting button 372 is operated, a setting region 375 is displayed in the image display region 394 and the user sets a region by moving the setting region 375.

The luminance information input region 373 includes a red luminance adjustment bar 373R for inputting luminance information of red, a green luminance adjustment bar 373G for inputting luminance information of green, and a blue luminance adjustment bar 373B for inputting luminance information of blue. When one of the adjustment bards 373R, 373G and 373B is operated, other adjustment bars are also operated and thus luminance information is input such that intensities of the three colors become constant. Further, the adjustment bars 373R, 373G and 373B may be separately adjusted, and when they are separately adjusted, the emission intensity of the lighting apparatus 4 is adjusted such that luminance information of each color extracted from image data corresponds to each piece of input luminance information.

The adjustment initiation button 374 is a button for initiating adjustment of the emission intensity of the lighting apparatus 4 in response to information input to the reference color setting region 370. Meanwhile, when information necessary to initiate adjustment has not been input yet when the adjustment initiation button 374 is operated, information indicating an error may be displayed to prompt input of the information. Here, the information necessary to initiate adjustment is information about a region set for luminance information and image data.

A user interface for realizing the third adjustment function will be described with reference to FIG. 12.

The search setting region 380 includes a display switch icon 381, a first region setting button 382, a second region setting button 384, and a search initiation button 386.

The display switch icon 381 is an icon for switching display and non-display of the first region setting button 382, the second region setting button 384 and the search initiation button 386.

The first region setting button 382 and the second region setting button 384 are buttons for setting two regions for which a user wants to maximize contrast. When the first region setting button 382 is operated, a first setting region 383 is displayed in the image display region 394, and the user sets a region by moving the first setting region 383. When the second region setting button 384 is operated, a second setting region 385 is displayed in the image display region 394 and the user sets a region by moving the second setting region 385 in the same manner.

The search initiation button 386 is a button for initiating search for an emission state in which the contrast between two regions input to the search setting region 380 is maximized. Meanwhile, when information necessary to initiate the search has not been input yet when the search initiation button 386 is operated, information indicating an error may be displayed to prompt input of the information necessary to initiate the search.

[H. Functional Configuration of Control Program 150]

Figure 13:
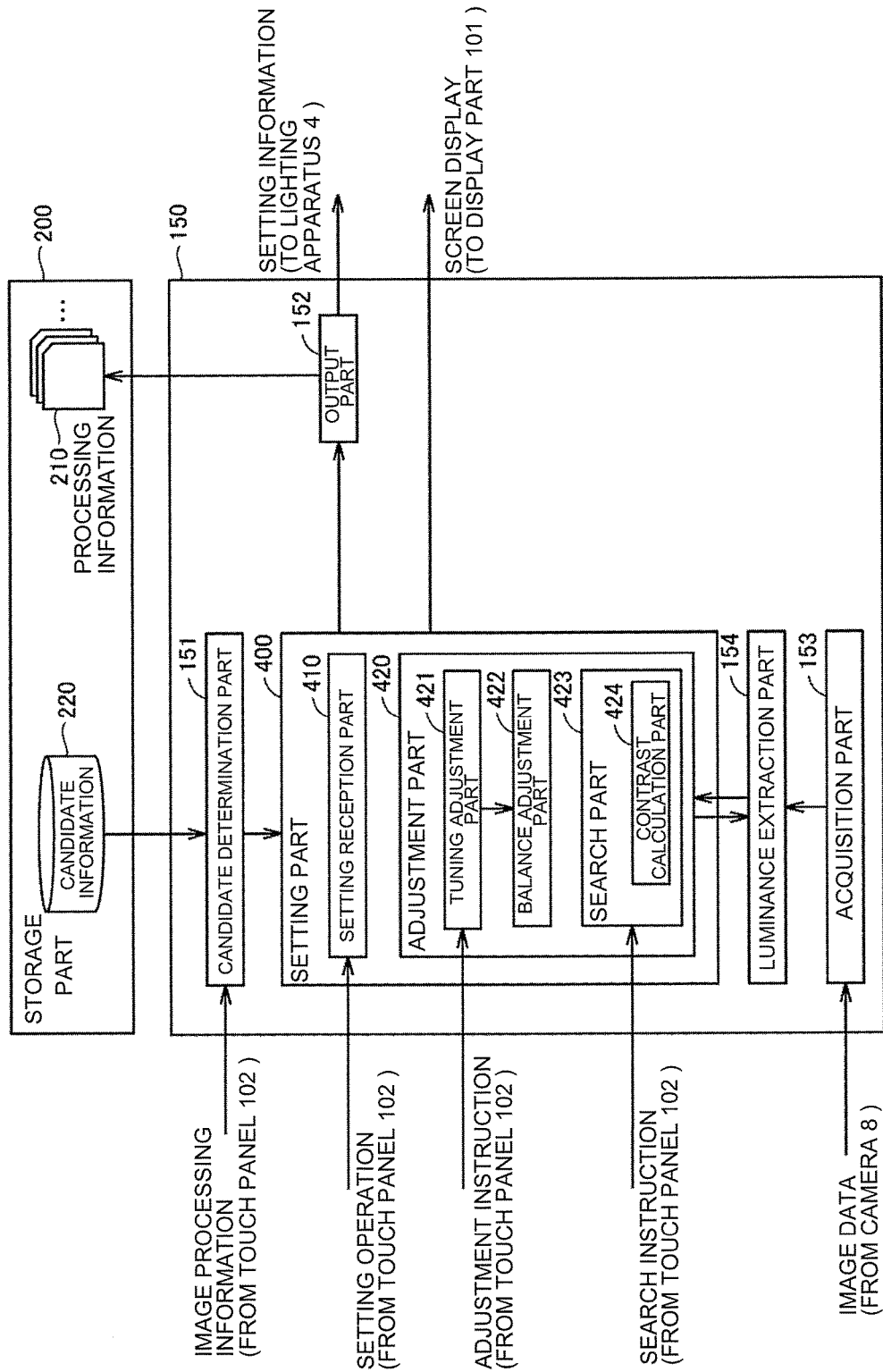
FIG. 13 is a schematic diagram illustrating a configuration of a control program.

Next, a functional configuration of the control program 150 for realizing user interfaces described with reference to FIG. 6 to FIG. 12 will be described with reference to FIG. 13. FIG. 13 is a schematic diagram illustrating a configuration of the control program 150.

The control program 150 includes a candidate determination part 151, a setting part 400, an output part 152, an acquisition part 153 and a luminance extraction part 154 as basic functional configurations.

The candidate determination part 151 determines lighting-up region candidates and emission state candidates to be presented on the basis of image processing information input through the touch panel 102 and candidate information 220 stored in a storage part 200. The image processing information is information representing details of image processing, and specifically, the image processing information is information input on the basis of selection of one of buttons included in the image processing details reception region 340 (refer to FIG. 6). The candidate information 220 is information in which candidates presented for each piece of image processing information are stored. The candidate determination part 151 sends information representing determined lighting-up region candidates and emission state candidates to the setting part 400.

The setting part 400 provides the user interface 300 for performing lighting-up setting. That is, the setting part 400 displays the user interface 300 as shown in FIG. 6 to FIG. 12 to the display part 101 and generates setting information representing details of lighting-up setting performed according to user operation. The setting part 400 sends the generated setting information to the output part 152.

The setting part 400 includes a setting reception part 410 and an adjustment part 420.

The setting reception part 410 accepts setting for the lighting apparatus 4 in response to a setting operation of the user and generates setting information. For example, when the user designates a lighting-up region candidate and an emission state candidate through the candidate selection region 350 (refer to FIG. 6), the setting reception part 410 accepts the designation, displays accepted details on the display part 101, generates setting information and outputs the setting information to the output part 152.

The adjustment part 420 adjusts the emission state of the lighting apparatus 4 on the basis of image data generated by the camera 8. The adjustment part 420 includes a tuning adjustment part 421, a balance adjustment part 422, and a search part 423. Further, the adjustment part 420 instructs the luminance extraction part 154 to acquire luminance information from image data and receives a luminance value extracted by the luminance extraction part 154.

The tuning adjustment part 421 and the balance adjustment part 422 adjusts the emission state of the lighting apparatus 4 on the basis of an adjustment instruction from the touch panel 102. Here, the adjustment instruction is output on the basis of reception of an operation of the adjustment initiation button 374 included in the reference color setting region 370. The adjustment part 420 transmits information which specifies a region set for image data included in the adjustment instruction to the luminance extraction part 154 and instructs the luminance extraction part 154 to extract the average of luminance each color of the region.

The tuning adjustment part 421 is a functional component in charge of the first adjustment function. The tuning adjustment part 421 calculates a difference between a luminance value input to the luminance information input region 373 and the average of luminance each color acquired from the luminance extraction part 154, generates setting information through which the difference decreases, and sends the setting information to the output part 152. The tuning adjustment part 421 repeats generation of setting information and transmission of the setting information to the output part 152 until the difference between the luminance value input to the luminance information input region 373 and the average of luminance each color acquired from the luminance extraction part 154 decreases below a predetermined threshold value. In addition, the tuning adjustment part 421 instructs the balance adjustment part 422 to adjust the balance between brightnesses of each color on the basis of decrease of the difference below the predetermined threshold value. Further, it is desirable that the tuning adjustment part 421 repeat generation of setting information and transmission of the setting information to the output part 152 at least until a luminance value of one of all colors extracted from the image data becomes a value close to the luminance value input to the luminance information input region 373.

The balance adjustment part 422 is a functional component in charge of the second adjustment function. The balance adjustment part 422 adjusts the balance between brightnesses of each color from a luminance value of each color transmitted from the luminance extraction part 154. Specifically, the balance adjustment part 422 generates setting information from luminance each color transmitted from the luminance extraction part 154 such that luminance each color become identical and transmits the setting information to the output part 152. Here, the balance adjustment part 422 generates setting information such that the luminance value of one color which has become a value close to the luminance value input to the luminance information input region 373 by the tuning adjustment part 421 does not change. The balance adjustment part 422 repeats calculation of a luminance value difference of each color, generation of setting information and transmission of the setting information to the output part 152 until a luminance value difference of each color decreases below a predetermined threshold value. The balance adjustment part 422 instructs the output part 152 to output the setting information to the storage part 200 on the basis of decrease of the luminance value difference of each color below the predetermined threshold value.

The search part 423 is a functional component in charge of the third adjustment function. The search part 423 searches for an emission state of an emission part in which the contrast between brightnesses of two regions specified for image data increases on the basis of a search instruction from the touch panel 102. Here, the search instruction is an instruction output on the basis of reception of an operation of the search initiation button 386 included in the search setting region 380. The adjustment part 420 transmits information which specifies two regions set for the image data included in the search instruction to the luminance extraction part 154 and instructs the luminance extraction part 154 to extract the average of luminance each color for each of the two regions.

The search part 423 includes a contrast calculation part 424. The contrast calculation part 424 calculates a difference between averages of luminance the two regions transmitted from the luminance extraction part 154 as a contrast. The search part 423 changes setting the lighting apparatus 4, calculates a contrast for each setting value, and calculates a setting value which maximizes a contrast. The search part 423 outputs the setting value which maximizes the contract to the output part 152 as setting information and instructs the output part 152 to output the setting information to the storage part 200. The search part 423 searches lighting-up region candidates and emissions state candidates determined by the candidate determination part 151.

The output part 152 outputs the transmitted setting information to the lighting apparatus 4. In addition, the output part 152 stores the setting information in the storage part 200 on the basis of an instruction of the setting part 400.

[I. Candidate Information]

Next, referencing to FIG. 14, the candidate information 220 is referred by the candidate determination part 151. FIG. 14 is a diagram illustrating a data structure of the candidate information 220.

As shown in FIG. 14, the candidate information 220 is information indicating whether a candidate among a plurality of candidates is presented. The information indicating whether a candidate among a plurality of candidates is presented is stored for each piece of image processing information. The candidate determination part 151 extracts candidate information 220 of image processing information which corresponds to input image processing information and outputs the candidate information 220 to the setting part 400.

Image processing information includes information indicating a purpose of image processing and information indicating properties of a workpiece W. For example, the information indicating the purpose of image processing includes "roughness," "contamination" and the like. For example, the information indicating properties of a workpiece W includes "red," "reflectivity: high" and the like. Here, "red" is the color of the workpiece W.

The image processing information shown in FIG. 14 is an example, and the image processing apparatus 100 may store candidate information based on other pieces of information in the storage part 200. Further, the storage part 200 may be provided in a server which can communicate with the image processing apparatus 100, instead of the image processing apparatus 100.

[J. Flowchart]

Figure 15:
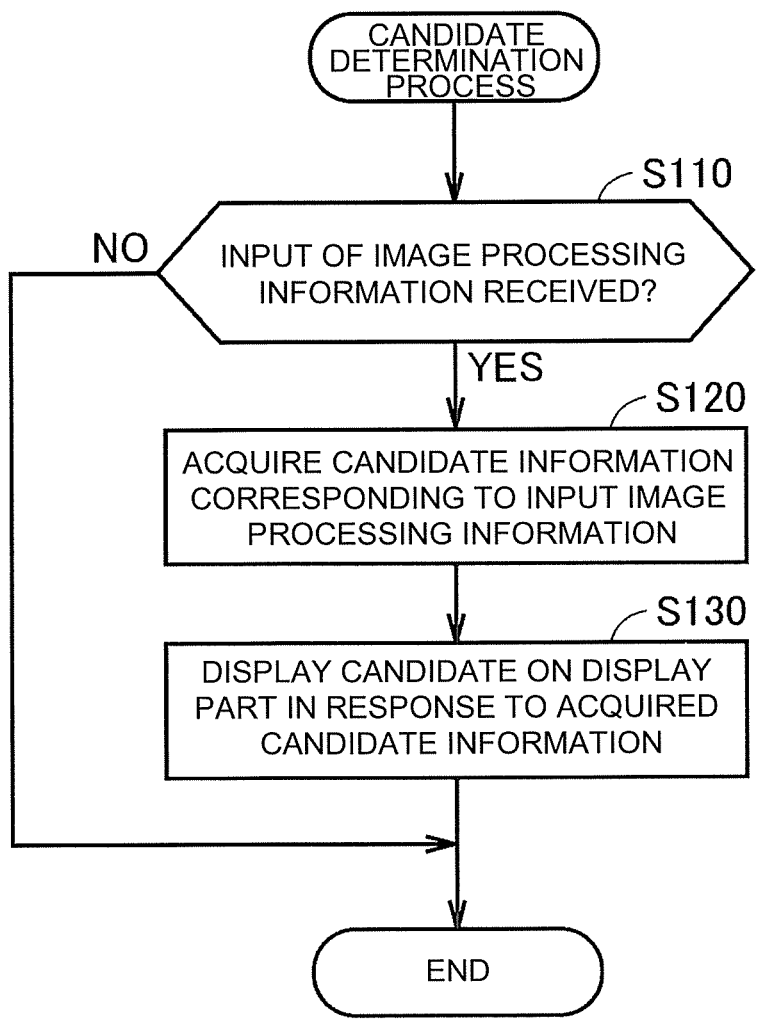
FIG. 15 is a flowchart of a candidate determination process.
Figure 16:
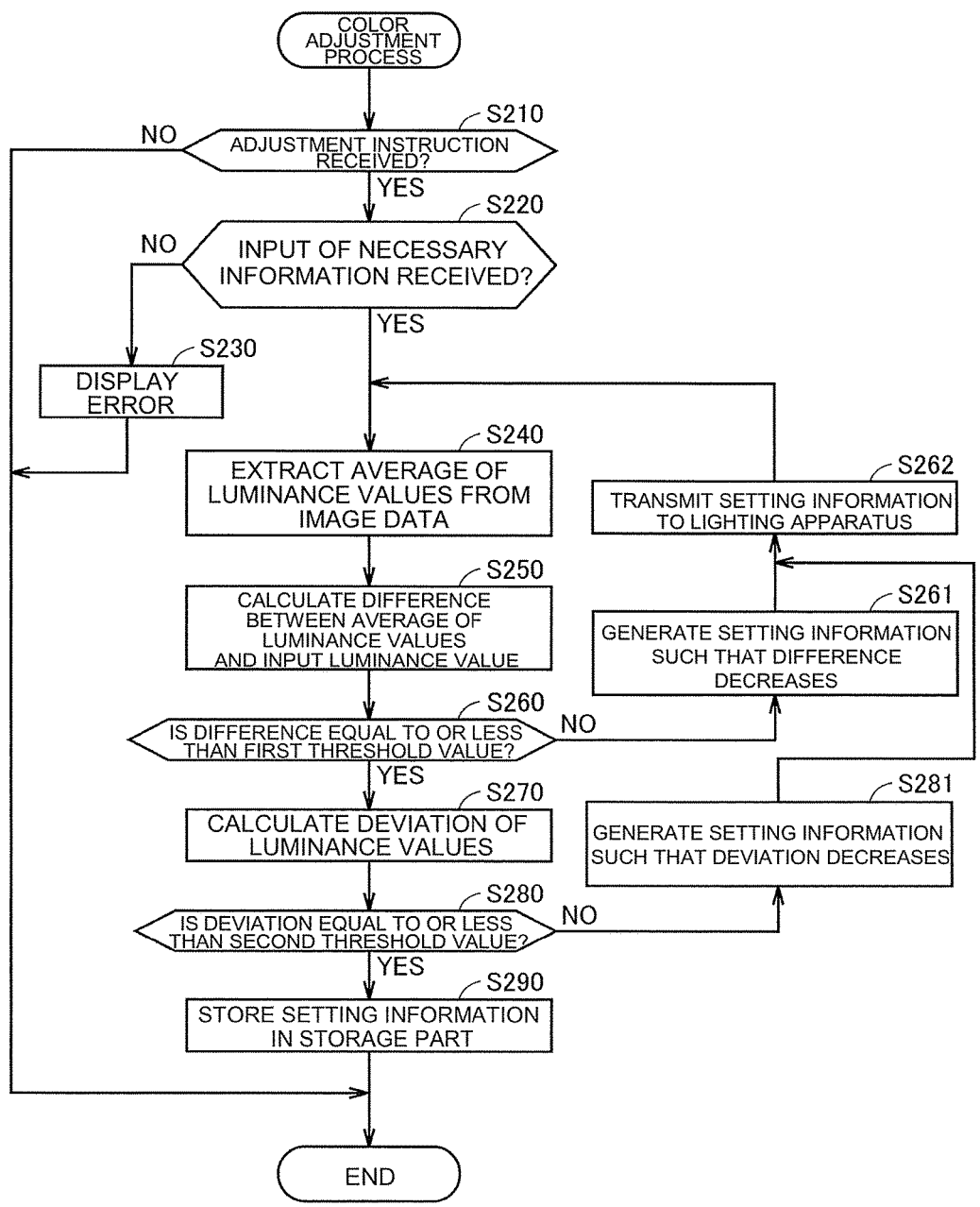
FIG. 16 is a flowchart of an adjustment process.
Figure 17:
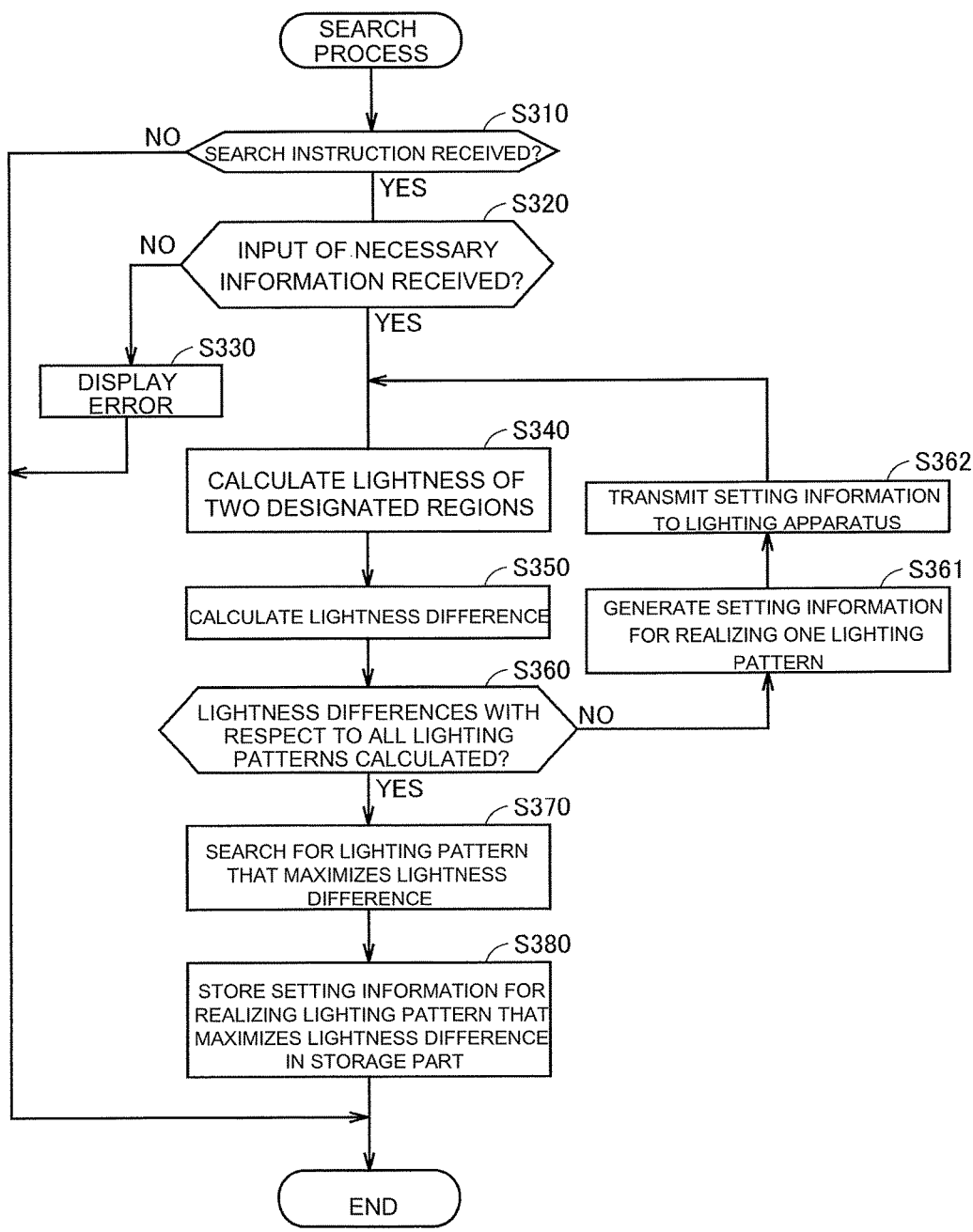
FIG. 17 is a flowchart of a search process.

A control structure of the image processing system 1 will be described with reference to FIGS. 15 to 17. FIG. 15 is a flowchart illustrating a candidate determination process performed by the image processing apparatus 100 to determine candidates to be presented. FIG. 16 is a flowchart illustrating an adjustment process executed by the image processing apparatus 100 to adjust an emission state on the basis of an adjustment instruction. FIG. 17 is a flowchart of a search process executed by the image processing apparatus 100 to search for an emission state in which the contrast between two regions set for image data is maximized on the basis of a search instruction.

[J1. Candidate Determination Process]

First, the candidate determination process executed by the image processing apparatus 100 will be described with reference to FIG. 15. The candidate determination process is executed when the user selects any one of the buttons included in the image processing details reception region 340. For example, the process shown in FIG. 15 is realized by executing a program by the processor 110 of the image processing apparatus 100 (refer to FIG. 2). In another embodiment, part of or whole process may be executed by other hardware devices.

In step S110, the processor 110 determines whether input of image processing information has been received. When it is determined that input of the image processing information has been received (YES in step S110), the processor 110 switches the control to step S120. When it is determined that input of the image processing information has not been received (NO in step S110), the processor 110 ends the process. When the user selects any button included in the image processing details reception region 340, the processor 110 determines that input of the image processing information has been received.

In step S120, the processor 110 acquires candidate information 220 corresponding to the input image processing information.

In step S130, the processor 110 presents candidates in response to the acquired candidate information 220 in the display part 101 and ends the process. For example, the processor 110 displays buttons corresponding to candidate targets in a different state from buttons other than the candidate targets, as shown in FIG. 6 or FIG. 7.

[J2. Adjustment Process]

Next, the adjustment process executed by the image processing apparatus 100 will be described with reference to FIG. 16. The adjustment process is executed when the user inputs information necessary for the adjustment process and then operates the adjustment initiation button 374. For example, the process shown in FIG. 16 is realized by executing a program by the processor 110 of the image processing apparatus 100 (refer to FIG. 2). In another embodiment, part of or all of the process may be executed by other hardware devices.

In step S210, the processor 110 determines whether an adjustment instruction has been received. When it is determined that the adjustment instruction has been received (YES in step S210), the processor 110 switches the control to step S220. When it is determined that the adjustment instruction has not been received (NO in step S210), the processor 110 ends the process. The adjustment instruction is sent to the processor 110 by operating the adjustment initiation button 374 by the user.

In step S220, the processor 110 determines whether input of information necessary for the adjustment process has been received. When it is determined that input of the information necessary for the adjustment process has been received (YES in step S220), the processor 110 switches the control to step S240. When it is determined that input of the information necessary for the adjustment process has not been received (NO in step S220), the processor 110 switches the control to step S230.

In step S230, the processor 110 displays an error and ends the process. For example, display of an error is a display for notifying the user that input of the information necessary for the adjustment process has not been input and is a display of a text image such as "Please, designate a region or input luminance information."

In step S240, the processor 110 extracts the average of luminance values with respect to each color in a designated region from image data. The average of luminance values may be calculated from pixel values included in the designated region.

In step S250, the processor 110 calculates a difference between the average of luminance values and an input luminance value for each color.

In step S260, the processor 110 determines whether a smallest difference among differences calculated for colors is equal to or less than a first threshold value.

When it is determined that the difference is equal to or less than the first threshold value (YES in step S260), the processor 110 switches the control to step S270. When it is determined that the difference is not equal to or less than the first threshold value (NO in step S260), the processor 110 switches the control to step S261.

In step S261, the processor 110 generates setting information such that a luminance value difference decreases. In step S260, although it is desirable that the luminance value difference is the luminance value difference of the color determined to have the smallest difference, luminance value differences other colors may be used.

In step S262, the processor 110 sends the setting information to the lighting apparatus 4 and returns the control to step S240. The lighting apparatus 4 controls an emission state on the basis of the setting information sent thereto. The processor 110 repeats the process of step S240 to step S260 until the difference is determined to be equal to or less than the first threshold value.

In step S270, the processor 110 calculates a luminance value deviation. The luminance value deviation is a degree to which luminance other colors are deviated from the luminance value of the color determined to have a difference equal to or less than the first threshold value in step S260.

In step S280, the processor 110 determines whether the deviation is equal to or less than a predetermined second threshold value. When it is determined that the deviation is equal to or less than the second threshold value (YES in step S280), the processor 110 stores the setting information in the storage part 200 in step S290 and ends the process. When it is determined that the deviation is not equal to or less than the second threshold value (NO in step S280), the processor 110 switches the control to step S281.

In step S281, the processor 110 generates setting information such that the deviation decreases and switches the control to step S262. It is desirable that the processor 110 generate setting information such that the luminance value of the color determined to have a difference equal to or less than the first threshold value in step S260 is not changed in step S281.

The processor 110 repeats the process of step S240 to step S280 until it is determined that the deviation is equal to or less than the second threshold value.

[J3. Search Process]

Next, the search process executed by the image processing apparatus 100 will be described with reference to FIG. 17. The search process is executed when the user inputs information necessary for the search process and then operates the search initiation button 386. For example, the process shown in FIG. 17 is realized by executing a program by the processor 110 of the image processing apparatus 100 (refer to FIG. 2). In another embodiment, part of or whole process may be executed by other hardware devices.

In step S310, the processor 110 determines whether a search instruction has been received. When it is determined that the search instruction has been received (YES in step S310), the processor 110 switches the control to step S320. When it is determined that the search instruction has not been received (NO in step S310), the processor 110 ends the process. The search instruction is sent to the processor 110 when the user operates the search initiation button 386.

In step S320, the processor 110 determines whether information necessary for the search process has been received. When it is determined that input of the information necessary for the search process has been received (YES in step S320), the processor 110 switches the control to step S340. When it is determined that input of the information necessary for the search process has not been received (NO in step S320), the processor 110 switches the control to step S330.

In step S330, the processor 110 displays an error and ends the process. For example, display of an error is a display for notifying the user that input of the information necessary for the search process has not been input and is a display of a text image such as "Please, designate a region."

In step S340, the processor 110 extracts information about the brightness (lightness) of designated two regions from image data. For example, the lightness is a total sum of luminance each color included in pixel values.

In step S350, the processor 110 calculates a difference between the extracted lightnesses of the two regions.

In step S360, the processor 110 determines whether lightness differences have been calculated for all of selectable lighting patterns. Here, selectable lighting patterns are lighting patterns which can be selected according to candidates determined in the candidate determination process.

When it is determined that lightness differences have been calculated for all lighting patterns (YES in step S360), the processor 110 switches the control to step S370. When it is determined that lightness differences have not been calculated for all lighting patterns (NO in step S360), the processor 110 switches the control to step S361.

In step S361, the processor 110 generates setting information for realizing one of lighting patterns for which lightness differences have not been calculated.

In step S362, the processor 110 sends the setting information to the lighting apparatus 4 and returns the control to step S340. The lighting apparatus 4 controls an emission state on the basis of the setting information sent thereto. The processor 110 repeats the process of step S340 to step S360 until it is determined that lightness differences have been calculated for all lighting patterns.

In step S370, the processor 110 searches for a lighting pattern corresponding to a largest lightness difference among all of the calculated lightness differences.

In step S380, the processor 110 stores setting information for realizing the lighting pattern corresponding to the largest lightness difference in the storage part 200 and ends the process.

[Modified Examples]

[K. Adjustment Setting Region]

Figure 18:
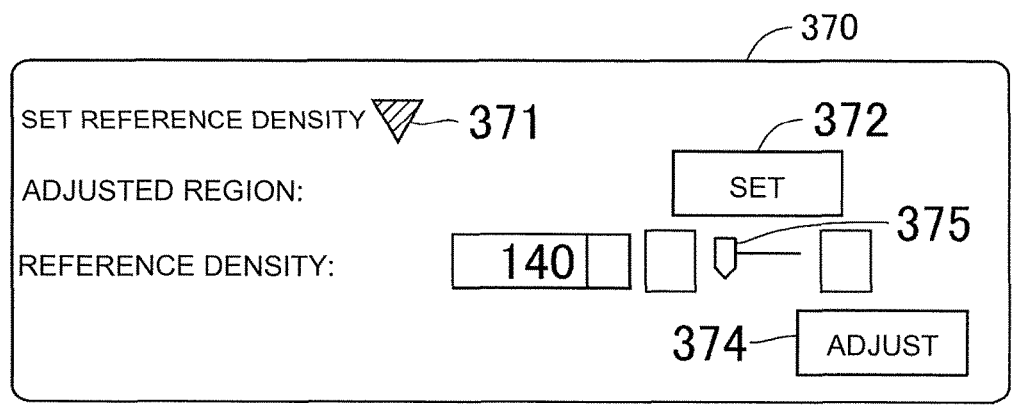
FIG. 18 is a diagram illustrating a modified example of an adjustment region.

Although the camera 8 can generate full-color image data in the present embodiment, the camera 8 may generate monochrome image data. A modified example of the reference color setting region 370 when the camera 8 generates monochrome image data will be described with reference to FIG. 18. FIG. 18 is a diagram illustrating a modified example of the adjustment setting region.

As shown in FIG. 18, only one adjustment bar 375 is provided. When the user inputs information necessary for the adjustment process by operating the adjustment bar 375 and the region setting button 372 and then presses the adjustment initiation button 374, the image processing apparatus 100 adjusts an emission state such that a difference from an input reference density becomes equal to or less than a first threshold value using the tuning adjustment part 421.

[L. Luminance Adjustment Region]

In the present embodiment, an example in which a luminance adjustment bar is provided in the luminance adjustment region 360 and luminance, i.e. the brightness of lighting, is controlled by moving the adjustment bar is exemplified with respect to luminance adjustment. A configuration in which a plurality of luminance candidates are presented as emission state candidates may be employed with respect to luminance.

Figure 19:
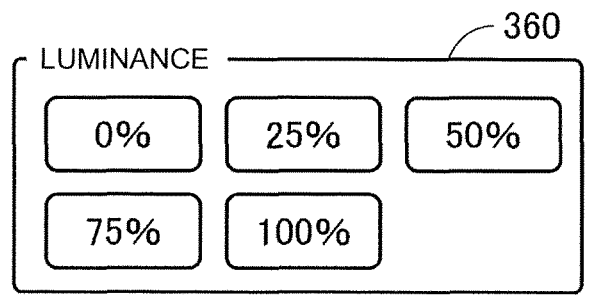
FIG. 19 is a diagram illustrating a modified example of a luminance adjustment region.

FIG. 19 is a diagram illustrating a modified example of the luminance adjustment region 360. As shown in FIG. 19, a plurality of luminance values may also be presented with respect to luminance.

[M. Setting Details Display Region]

Figure 20:
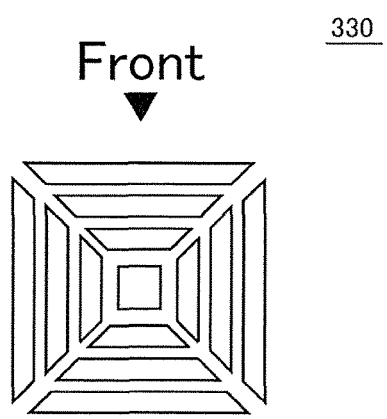
FIG. 20 is a diagram illustrating a modified example of a setting details display region.

In the present embodiment, regions are displayed in the same shapes as the shapes of regions set for light sources of the lighting apparatus 4 in the setting details display region 330. However, the regions set for the light sources of the lighting apparatus 4 displayed on the setting details display region 330 need not be completely consistent with the shapes of regions actually set for the light sources of the lighting apparatus 4. A plurality of regions displayed in the setting details display region 330 need to correspond to a plurality of regions actually set for the light sources of the lighting apparatus 4. For example, regions set for the light sources of the lighting apparatus 4 may be displayed in a square form as shown in FIG. 20.

[N. Regions Set for Light Sources of Lighting Apparatus]

Figure 21:
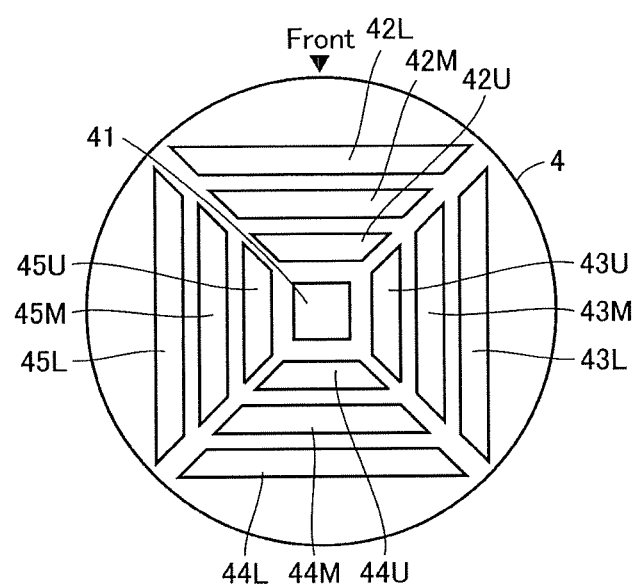
FIG. 21 is a diagram illustrating a modified example of a lighting apparatus.

Shapes of regions set for the light sources of the lighting apparatus 4 are assumed to be a circle as a whole in the present embodiment. Regions may be arbitrarily set for the light sources of the lighting apparatus 4 and shapes thereof are not limited. For example, regions may have a square form as a whole, as shown in FIG. 21.

In addition, a "ring shape" is desirably a shape having a hollow at the center and is not limited to a circular ring shape as in the present embodiment. For example, the "ring shape" may be a shape formed by hollowing the center of a square in a square form, like the upper region composed of the front region upper part 42U, the right region upper part 43U, the rear region upper part 44U and the left region upper part 45U of FIG. 21.

An "arc shape" is desirably a shape formed by dividing a ring shape into a plurality of regions and is not limited to a bow shape as in the present embodiment. For example, the "arc shape" may be a trapezoidal shape like the left region upper part 45U of FIG. 21.

In addition, although the central region 41 is a circular region in the present embodiment, the central region 41 may be a region positioned approximately at the center of the surface on which a light source is provided and the shape thereof is not limited to a circle. For example, the central region 41 may have a square shape as shown in FIG. 21. In addition, although the shape of the central region is associated with the shapes of ring-shaped regions in FIG. 2 and FIG. 21, the central region may have a square shape whereas the ring-shaped regions may have a ring shape, or the central region may have a circular shape whereas the ring-shaped regions may have a frame shape.

[Advantages]

As described above, the image processing apparatus 100 presents a plurality of lighting-up region candidates and emission state candidates to the user. Consequently, lighting pattern types of the lighting apparatus 4 are limited and choices are narrowed, and thus the user can perform lighting-up setting more easily.

In addition, the image processing apparatus 100 determines lighting-up region candidates and emission state candidates to be presented depending on details of image processing. Accordingly, a lighting pattern depending on the details of image processing can be easily selected, and image processing can be performed with higher accuracy.

Furthermore, since presented emission state candidates include colors specified according to the emission intensity of each light source type, lighting-up setting can be performed more easily than setting of the emission intensity for each light source type.

Moreover, lighting-up setting of the lighting apparatus 4 can be performed in consideration of the function of the camera 8 and optical properties of a target because the emission state of the lighting apparatus 4 can be adjusted using image data.

According to an embodiment, a setting assistance device allowing lighting-up setting to be performed for a lighting part having a plurality of light-emitting parts arranged at positions facing a target is provided. The setting assistance device includes: a first reception means which presents a plurality of lighting-up region candidates that define one or more predetermined regions among a plurality of regions set for the plurality of light-emitting parts and accepts designation of any lighting-up region candidate; a second reception means which presents a plurality of emission state candidates that define predetermined emission states of the light-emitting parts and accepts designation of any emission state candidate; and an output means which outputs lighting-up setting of the lighting part to the lighting part on the basis of designation of a lighting-up region candidate accepted by the first reception means and designation of an emission state candidate accepted by the second reception means.

According to an embodiment, the plurality of light-emitting parts arranged in the lighting part include light-emitting parts of a plurality of types having different dominant wavelengths. The plurality of emission state candidates presented by the second reception means include colors determined according to an emission intensity of each light-emitting part type.

According to an embodiment, the plurality of regions set in the plurality of light-emitting parts include a central region positioned at the center and one or more ring-shaped regions having different diameters and positioned having the central region as a center thereof. The plurality of lighting-up region candidates presented by the first reception means include candidates defined by the central region and the one or more ring-shaped regions.

According to an embodiment, the setting assistance device further includes an acquisition means which acquires image data generated by photographing at least some of irradiation regions of the lighting part through a photographing part, and an adjustment means which adjusts emission states of the light-emitting parts on the basis of the image data.

According to an embodiment, the setting assistance device further includes a means which accepts designation of a luminance value of the image data. The adjustment means includes a means which extracts a luminance value from the image data and adjusts emission states of the light-emitting parts such that a difference between the extracted luminance value and the input luminance value decreases.

According to an embodiment, the adjustment means includes a means which adjusts the emission states of the light-emitting parts in order to adjust a balance between brightnesses of each color acquired from the image data.

According to an embodiment, the setting assistance device further includes a means which accepts designation of a first region and a second region defined for the image data. The adjustment means includes a means which extracts information about brightnesses of each of the first region and the second region and searches for emission states of the light-emitting parts in which a contrast between brightnesses of the first region and the second region increases on the basis of the extracted information.

According to another embodiment, an image processing system includes: a photographing part which photographs a target; a lighting part having a plurality of light-emitting parts arranged at positions facing the target; a first reception means which presents a plurality of lighting-up region candidates that define one or more predetermined regions among a plurality of regions set for the plurality of light-emitting parts and accepts designation of any lighting-up region candidate; a second reception means which presents a plurality of emission state candidates that define predetermined emission states of the light-emitting parts and accepts designation of any emission state candidate; and an output means which outputs lighting-up settings of the lighting part to the lighting part on the basis of designation of a lighting-up region candidate accepted by the first reception means and designation of an emission state candidate accepted by the second reception means.

According to another embodiment, a setting assistance program for allowing lighting-up setting to be performed for a lighting part having a plurality of light-emitting parts arranged at positions facing a target is provided. The setting assistance program includes: a step of presenting a plurality of lighting-up region candidates that define one or more predetermined regions among a plurality of regions set for the plurality of light-emitting parts and accepting designation of any lighting-up region candidate; a step of presenting a plurality of emission state candidates that define predetermined emission states of the light-emitting parts and accepting designation of any emission state candidate; and a step of outputting lighting-up settings of the lighting part to the lighting part on the basis of the designated lighting-up region candidate and the designated emission state candidate.

The disclosed embodiments are to be construed in all aspects as illustrative and not restrictive. The scope of the disclosure should be determined by the appended claims and their legal equivalents, not by the above description, and all changes coming within the meaning and equivalency range of the appended claims are intended to be embraced therein. In addition, the embodiments and modified examples of the disclosure are intended to be embodied alone or in combination as long as possible.

What is claimed is:

1. A setting assistance device allowing lighting-up setting to be performed for a lighting part having a plurality of light-emitting parts arranged at positions facing a target, comprising a processor configured to:
   present a plurality of lighting-up region candidates that define one or more predetermined regions among a plurality of regions set for the plurality of light-emitting parts and accepts designation of any lighting-up region candidate;
   present a plurality of emission state candidates that define predetermined emission states of the light-emitting parts and accepts designation of any emission state candidate;
   output lighting-up settings of the lighting part to the lighting part on the basis of designation of a lighting-up region candidate accepted by the processor and designation of an emission state candidate accepted by the processor; and
   determine a lighting-up region candidate presented by the processor and an emission state candidate presented by the processor in response to designation of a type of processing for an image accepted by the processor.

2. The setting assistance device according to claim 1, wherein the plurality of light-emitting parts include light-emitting parts of a plurality of types having different dominant wavelengths, and
   the plurality of emission state candidates presented by the processor include colors determined according to an emission intensity of each light-emitting part type.

3. The setting assistance device according to claim 1, wherein the plurality of regions include a central region positioned at the center and one or more ring-shaped regions having different diameters and positioned having the central region as a center thereof, and
   the plurality of lighting-up region candidates presented by the processor include candidates defined by the central region and the one or more ring-shaped regions.

4. The setting assistance device according to claim 1, wherein the processor is further configured to:
   acquire image data generated by photographing at least some of irradiation regions of the lighting part through a photographing part; and
   adjust emission states of the light-emitting parts on the basis of the image data.

5. The setting assistance device according to claim 1, wherein the processor is further configured to:
   accept designation of the type of processing for the image acquired by photographing the target.

6. The setting assistance device according to claim 5, wherein the plurality of regions include a central region positioned at the center and one or more ring-shaped regions having different diameters and positioned having the central region as a center thereof, and
   the plurality of lighting-up region candidates presented by the processor include candidates defined by the central region and the one or more ring-shaped regions.

7. The setting assistance device according to claim 5, wherein the processor is further configured to:
   acquire image data generated by photographing at least some of irradiation regions of the lighting part through a photographing part; and
   adjust emission states of the light-emitting parts on the basis of the image data.

8. The setting assistance device according to claim 5, wherein the plurality of light-emitting parts include light-emitting parts of a plurality of types having different dominant wavelengths, and the plurality of emission state candidates presented by the processor include colors determined according to an emission intensity of each light-emitting part type.

9. The setting assistance device according to claim 8, wherein the processor is further configured to:
acquire image data generated by photographing at least some of irradiation regions of the lighting part through a photographing part; and
adjust emission states of the light-emitting parts on the basis of the image data.

10. The setting assistance device according to claim 8, wherein the plurality of regions include a central region positioned at the center and one or more ring-shaped regions having different diameters and positioned having the central region as a center thereof, and
the plurality of lighting-up region candidates presented by the processor include candidates defined by the central region and the one or more ring-shaped regions.

11. The setting assistance device according to claim 10, wherein the processor is further configured to:
acquire image data generated by photographing at least some of irradiation regions of the lighting part through a photographing part; and
adjust emission states of the light-emitting parts on the basis of the image data.

12. The setting assistance device according to claim 11, wherein the processor is further configured to accept designation of a first region and a second region defined for the image data,
wherein the processor extracts information about brightnesses of each of the first region and the second region and searches for emission states of the light-emitting parts in which the contrast between brightnesses of the first region and the second region increases on the basis of the extracted information.

13. The setting assistance device according to claim 11, wherein the processor adjusts the emission states of the light-emitting parts in order to adjust a balance between brightnesses of each color acquired from the image data.

14. The setting assistance device according to claim 13, wherein the processor is further configured to accept designation of a first region and a second region defined for the image data,
wherein the processor extracts information about brightnesses of each of the first region and the second region and searches for emission states of the light-emitting parts in which the contrast between brightnesses of the first region and the second region increases on the basis of the extracted information.

15. The setting assistance device according to claim 11, wherein the processor is further configured to accept designation of a luminance value of the image data,
wherein the processor extracts a luminance value from the image data and adjusts emission states of the light-emitting parts such that a difference between the extracted luminance value and the input luminance value decreases.

16. The setting assistance device according to claim 15, wherein the processor is further configured to accept designation of a first region and a second region defined for the image data,
wherein the processor extracts information about brightnesses of each of the first region and the second region and searches for emission states of the light-emitting parts in which the contrast between brightnesses of the first region and the second region increases on the basis of the extracted information.

17. The setting assistance device according to claim 15, wherein the processor adjusts the emission states of the light-emitting parts in order to adjust a balance between brightnesses of each color acquired from the image data.

18. The setting assistance device according to claim 17, wherein the processor is configured to accept designation of a first region and a second region defined for the image data,
wherein the processor extracts information about brightnesses of each of the first region and the second region and searches for emission states of the light-emitting parts in which the contrast between brightnesses of the first region and the second region increases on the basis of the extracted information.

19. An image processing system comprising:
a photographing part which photographs a target;
a lighting part having a plurality of light-emitting parts arranged at positions facing the target; and
a processor configured to:
present a plurality of lighting-up region candidates that define one or more predetermined regions among a plurality of regions set for the plurality of light-emitting parts and accepts designation of any lighting-up region candidate;
present a plurality of emission state candidates that define predetermined emission states of the light-emitting parts and accepts designation of any emission state candidate;
output lighting-up settings of the lighting part to the lighting part on the basis of designation of a lighting-up region candidate and designation of an emission state candidate; and
determine a lighting-up region candidate presented by the processor and an emission state candidate presented by the processor in response to designation of a type of processing for an image accepted by the processor.

20. A non-transitory computer-readable media, compressing setting assistance program for allowing lighting-up setting to be performed for a lighting part having a plurality of light-emitting parts arranged at positions facing a target, comprising:
presenting a plurality of lighting-up region candidates that define one or more predetermined regions among a plurality of regions set for the plurality of light-emitting parts and accepting designation of any lighting-up region candidate;
presenting a plurality of emission state candidates that define predetermined emission states of the light-emitting parts and accepting designation of any emission state candidate;
outputting lighting-up settings of the lighting part to the lighting part on the basis of the designated lighting-up region candidate and the designated emission state candidate; and
determining a light-up region candidate to be presented and an emission state candidate to be presented in response to designation of a type of processing for an image.

* * * * *